(12) United States Patent
Cao et al.

(10) Patent No.: US 11,029,419 B2
(45) Date of Patent: *Jun. 8, 2021

(54) RADIATION DETECTOR SUITABLE FOR A PULSED RADIATION SOURCE

(71) Applicant: SHENZHEN XPECTVISION TECHNOLOGY CO., LTD., Shenzhen (CN)

(72) Inventors: Peiyan Cao, Shenzhen (CN); Yurun Liu, Shenzhen (CN)

(73) Assignee: SHENZHEN XPECTVISION TECHNOLOGY CO., LTD., Shenzhen (CN)

( * ) Notice: Subject to any disclaimer, the term of this patent is extended or adjusted under 35 U.S.C. 154(b) by 128 days.

This patent is subject to a terminal disclaimer.

(21) Appl. No.: 16/170,545

(22) Filed: Oct. 25, 2018

(65) Prior Publication Data
US 2019/0064368 A1    Feb. 28, 2019

Related U.S. Application Data

(63) Continuation of application No. PCT/CN2016/102340, filed on Oct. 18, 2016.

(51) Int. Cl.
| | |
|---|---|
| *G01T 1/17* | (2006.01) |
| *H04N 5/32* | (2006.01) |
| *G01T 1/16* | (2006.01) |
| *G01T 7/00* | (2006.01) |

(Continued)

(52) U.S. Cl.
CPC .......... *G01T 1/17* (2013.01); *A61B 6/42* (2013.01); *G01T 1/16* (2013.01); *G01T 7/005* (2013.01); *H04N 5/32* (2013.01); *H04N 5/361* (2013.01)

(58) Field of Classification Search
CPC .. A61B 6/42; A61B 6/582; G01T 1/16; G01T 1/17; H04N 5/361
See application file for complete search history.

(56) References Cited

U.S. PATENT DOCUMENTS 4,063,097 A * 12/1977 Barrett ............... A61B 6/032
378/18
4,880,981 A    11/1989 Johnston
(Continued)

FOREIGN PATENT DOCUMENTS

| CN | 102805628 A | 12/2012 |
| CN | 105022082 A | 11/2015 |

(Continued)

*Primary Examiner* — Chih-Cheng Kao
(74) *Attorney, Agent, or Firm* — IPro, PLLC

(57) ABSTRACT

Disclosed herein is a radiation detector, comprising: a plurality of pixels, and a controller; wherein each pixel is configured to detect radiation emitted from a pulsed radiation source; wherein the pulsed radiation source is configured to emit radiation during a plurality of ON periods and configured not to emit radiation during a plurality of OFF periods; wherein the controller is configured to determine that the pulsed radiation source is at one of the ON periods or at one of the OFF periods; wherein the controller is configured to cause the pixels to integrate signals or not to integrate signals with determination that the radiation source is at one of the ON periods or at one of the OFF periods.

26 Claims, 25 Drawing Sheets

(51) Int. Cl.
*A61B 6/00* (2006.01)
*H04N 5/361* (2011.01)

(56) References Cited

U.S. PATENT DOCUMENTS

| | | | |
|---|---|---|---|
| 5,717,735 A * | 2/1998 | Ramsdell | A61B 6/0421 378/195 |
| 2002/0090058 A1* | 7/2002 | Yasuda | A61B 6/08 378/205 |
| 2002/0150210 A1* | 10/2002 | Stegehuis | A61B 6/481 378/95 |
| 2004/0001571 A1* | 1/2004 | Jahrling | A61B 6/4464 378/209 |
| 2004/0232949 A1 | 11/2004 | Arques | |
| 2005/0206769 A1* | 9/2005 | Kump | A61B 6/548 348/333.01 |
| 2009/0141860 A1* | 6/2009 | Ryge | G01T 1/2008 378/62 |
| 2009/0238330 A1 | 9/2009 | Luhta et al. | |
| 2010/0200757 A1* | 8/2010 | Sarin | A61B 6/42 250/361 R |
| 2012/0161016 A1* | 6/2012 | Schmitt | G01T 1/17 250/370.06 |
| 2012/0300904 A1* | 11/2012 | Shimada | A61B 6/542 378/62 |
| 2017/0374295 A1* | 12/2017 | Topfer | H04N 5/32 |

FOREIGN PATENT DOCUMENTS

| | | |
|---|---|---|
| CN | 105662443 A | 6/2016 |
| WO | 2016099617 A1 | 6/2016 |
| WO | 2016094503 A9 | 7/2017 |

* cited by examiner

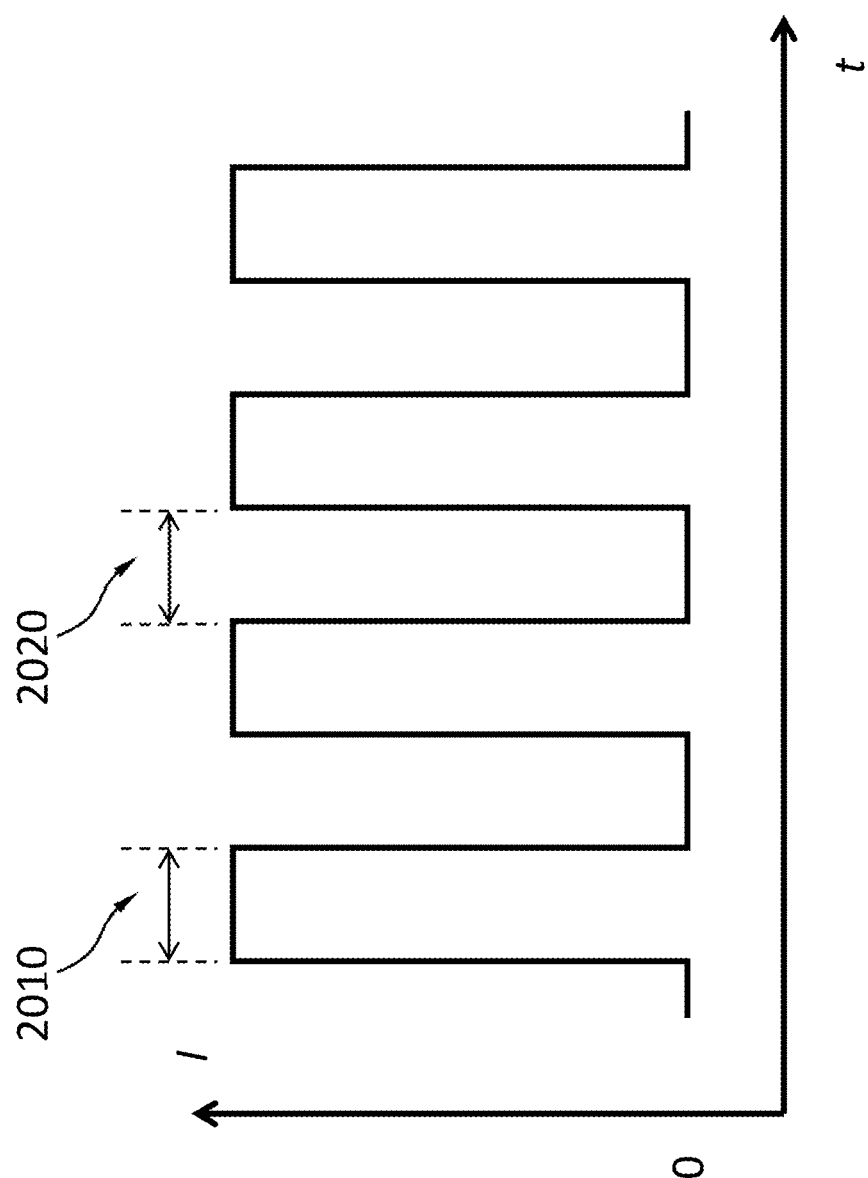

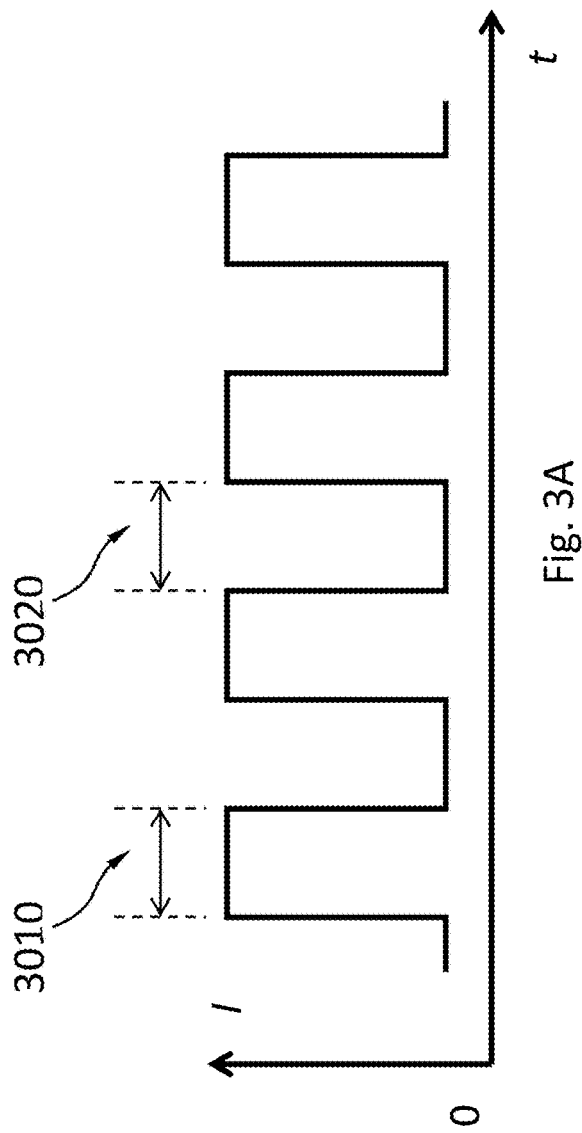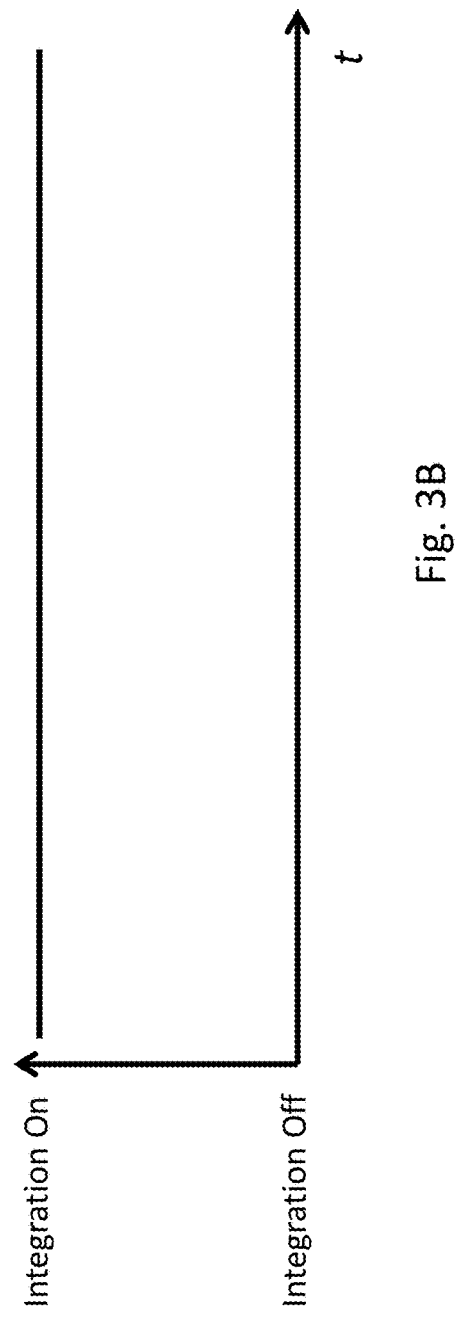

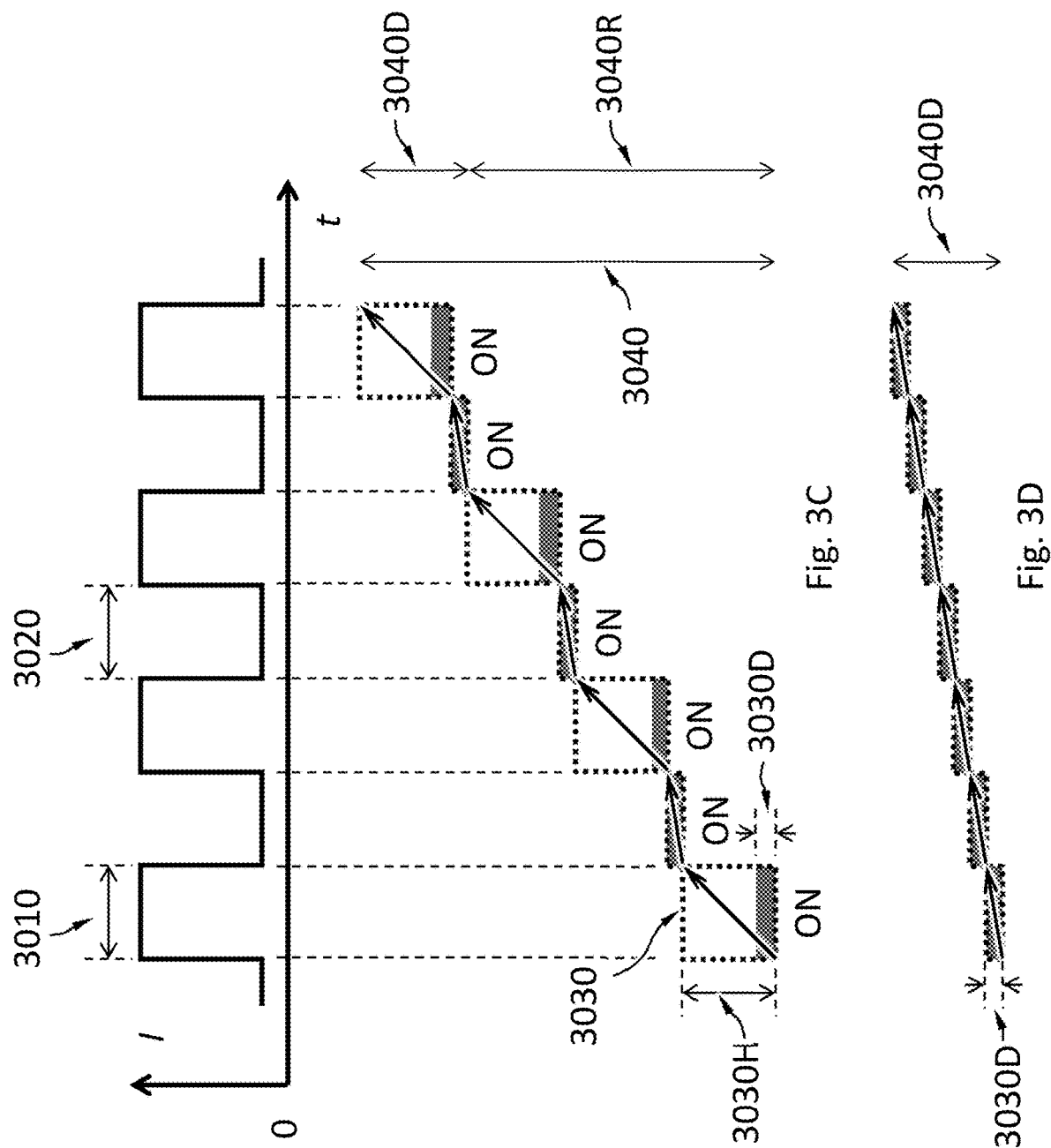

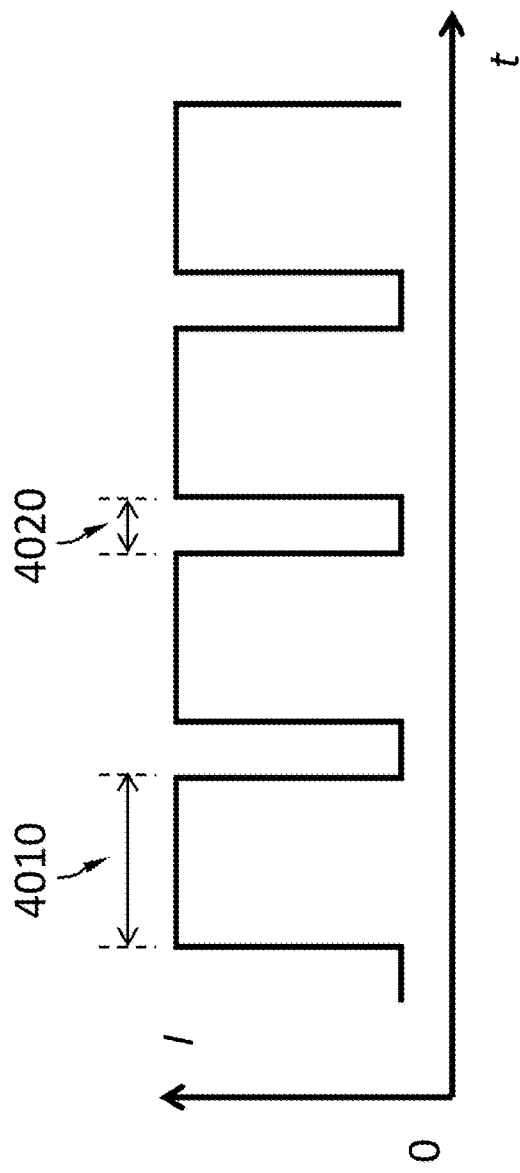
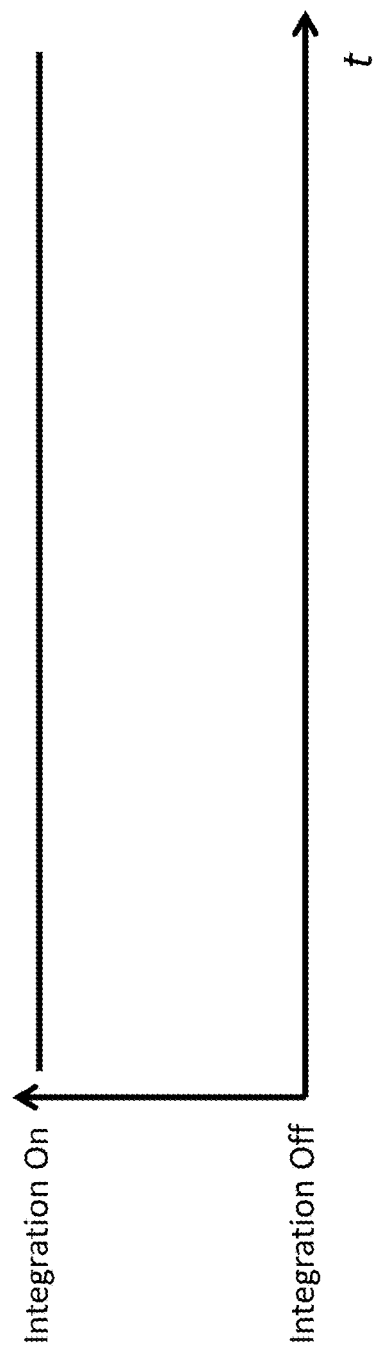
Fig. 4A
Fig. 4B

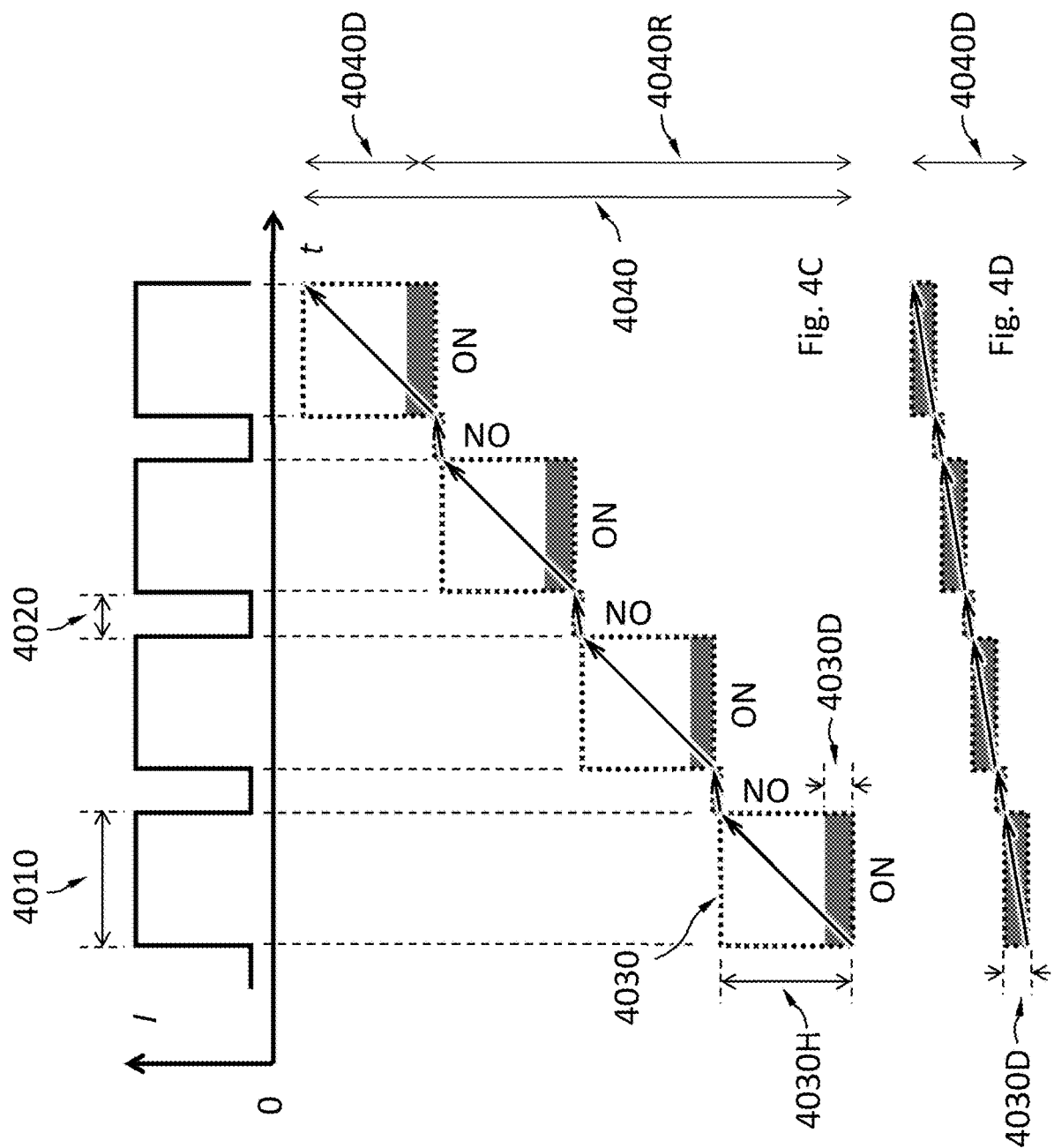

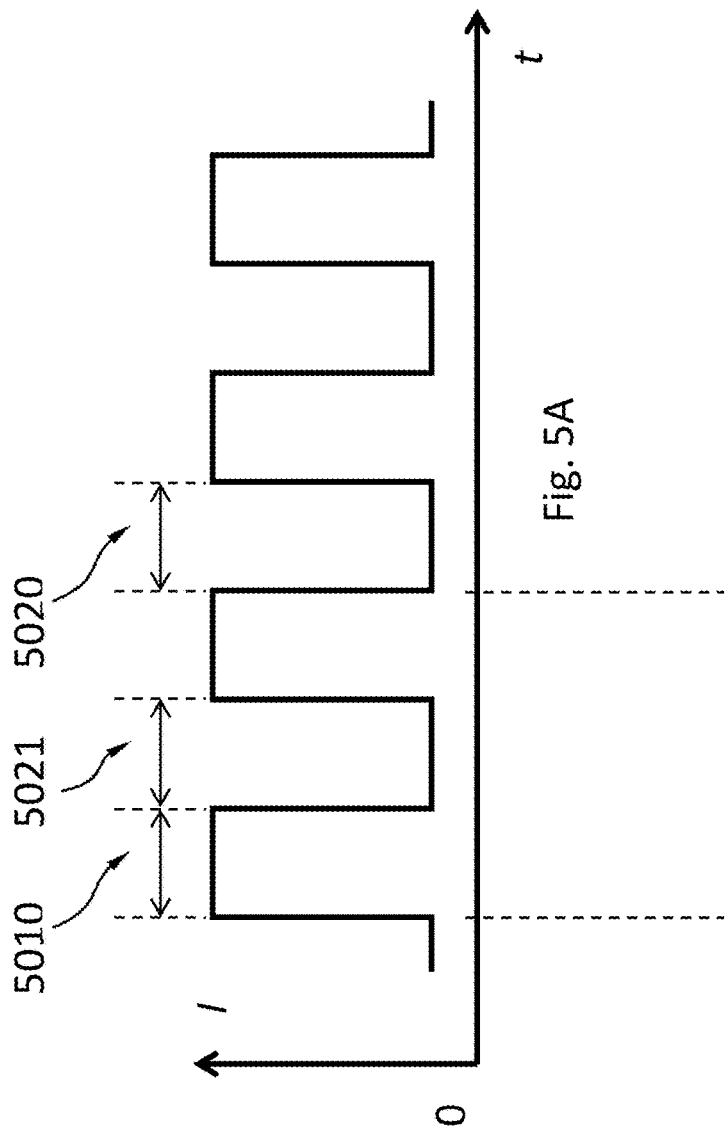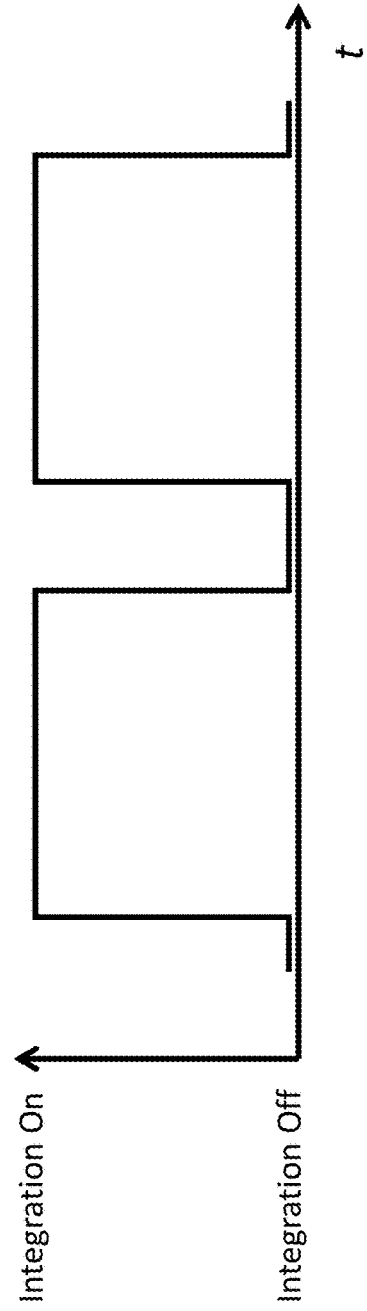

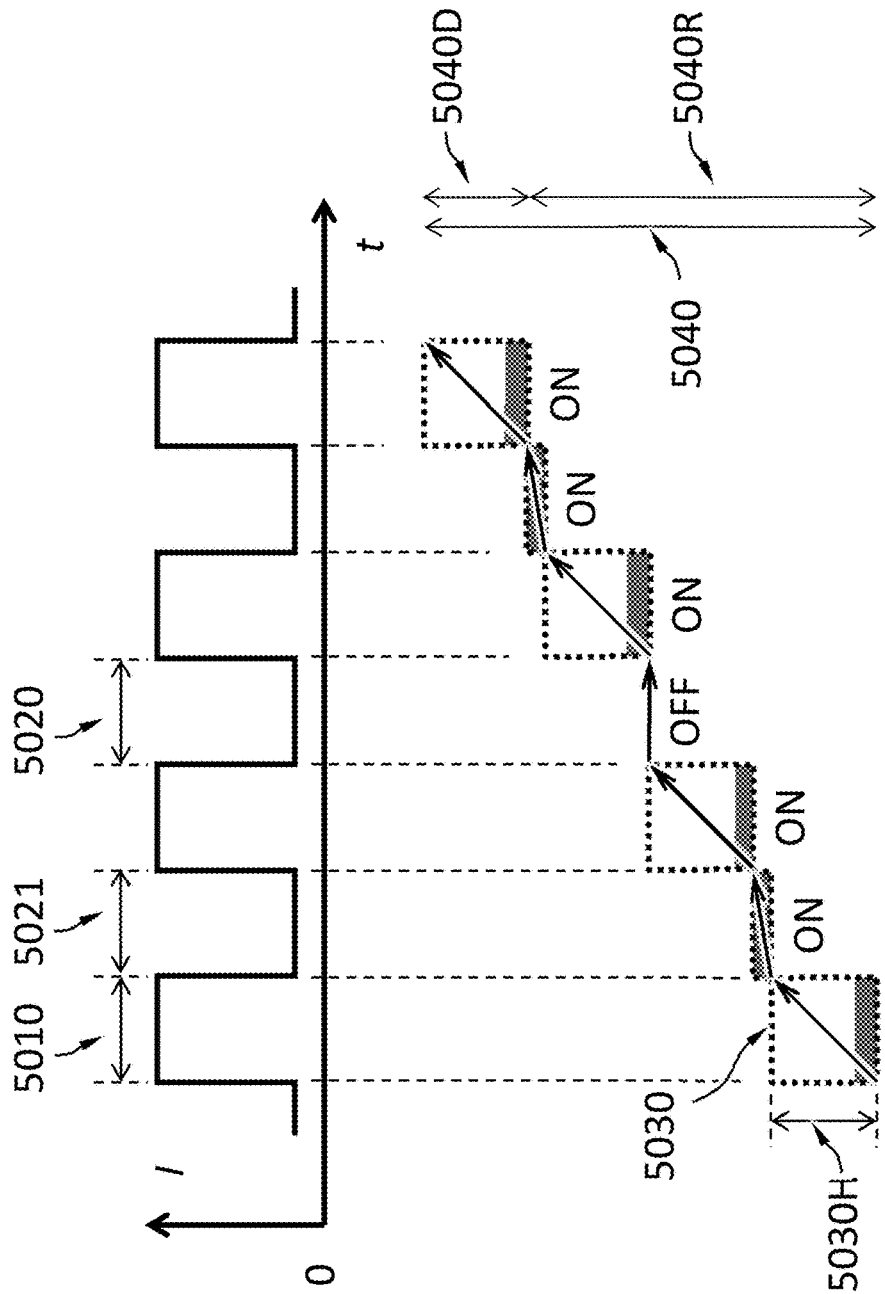

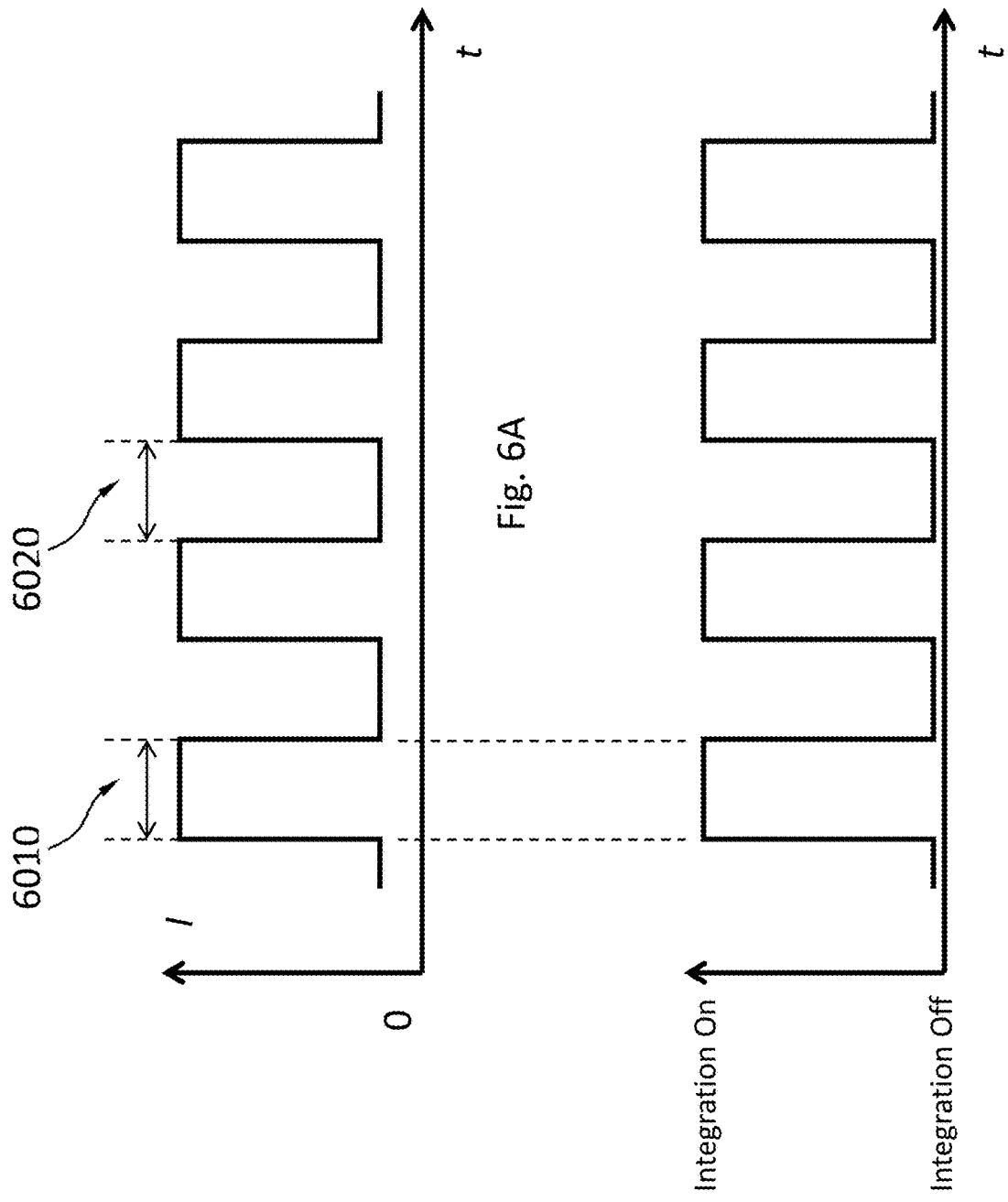

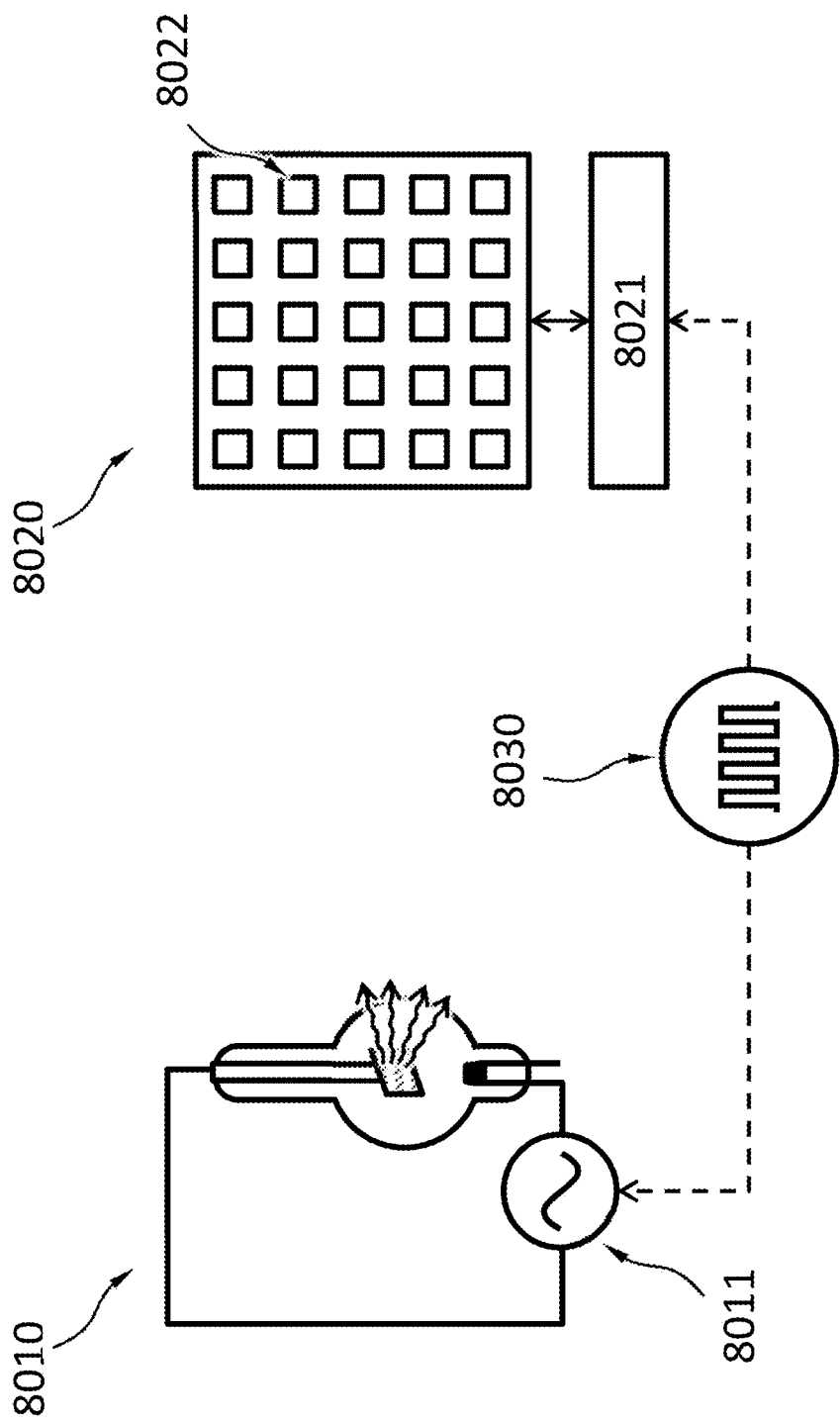

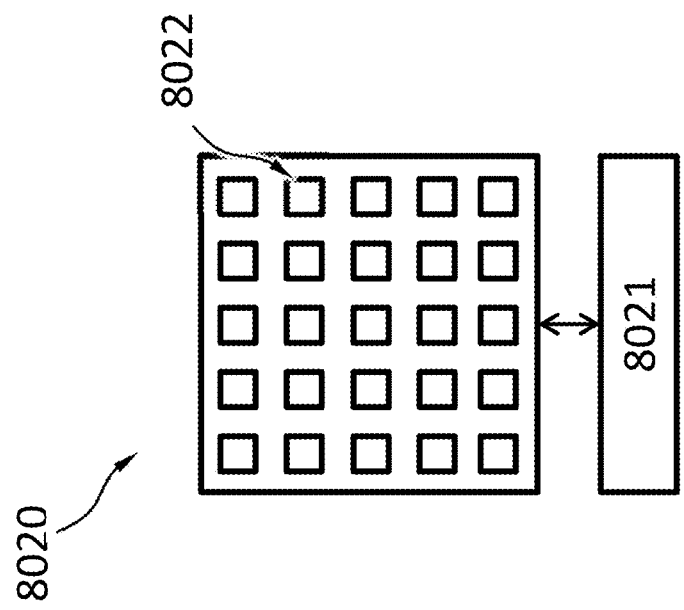
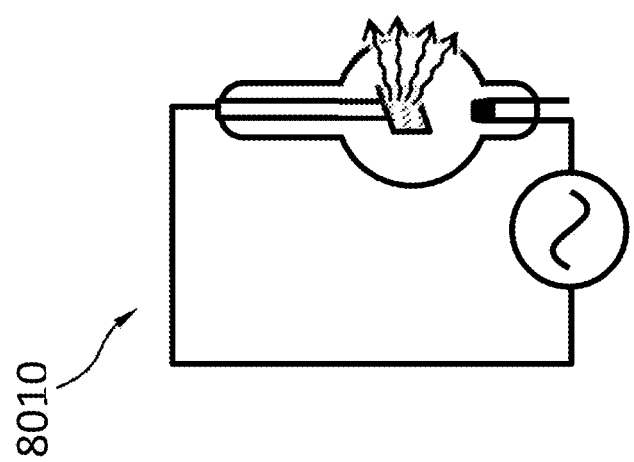
Fig. 9C

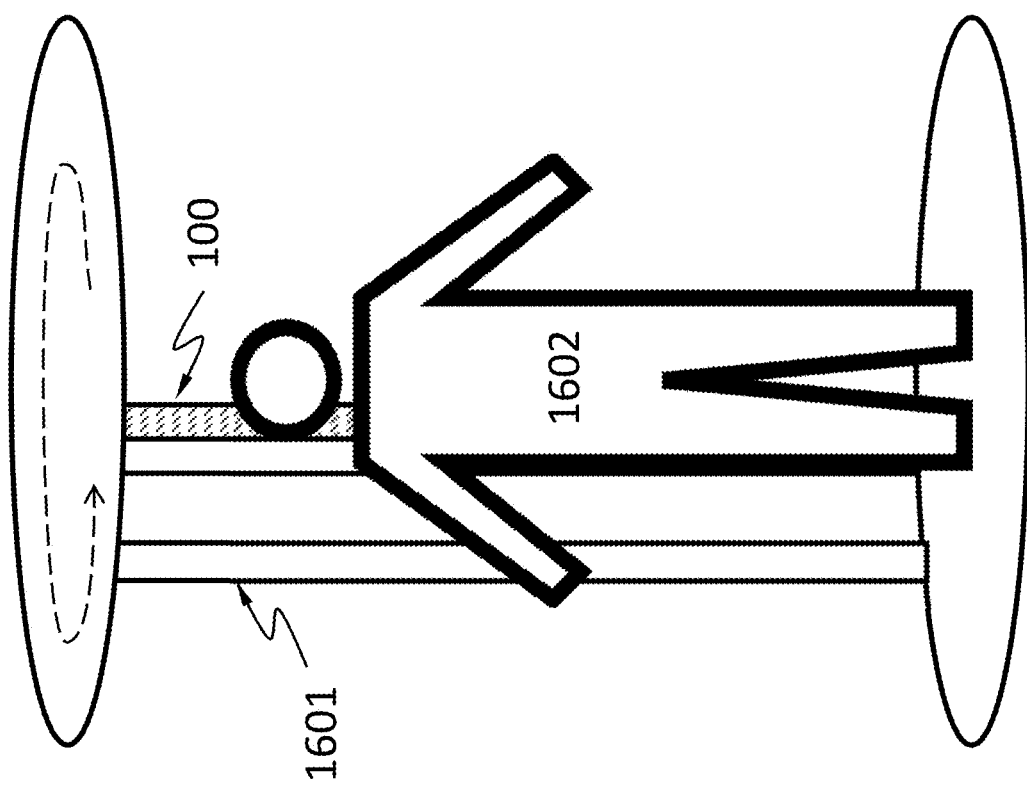

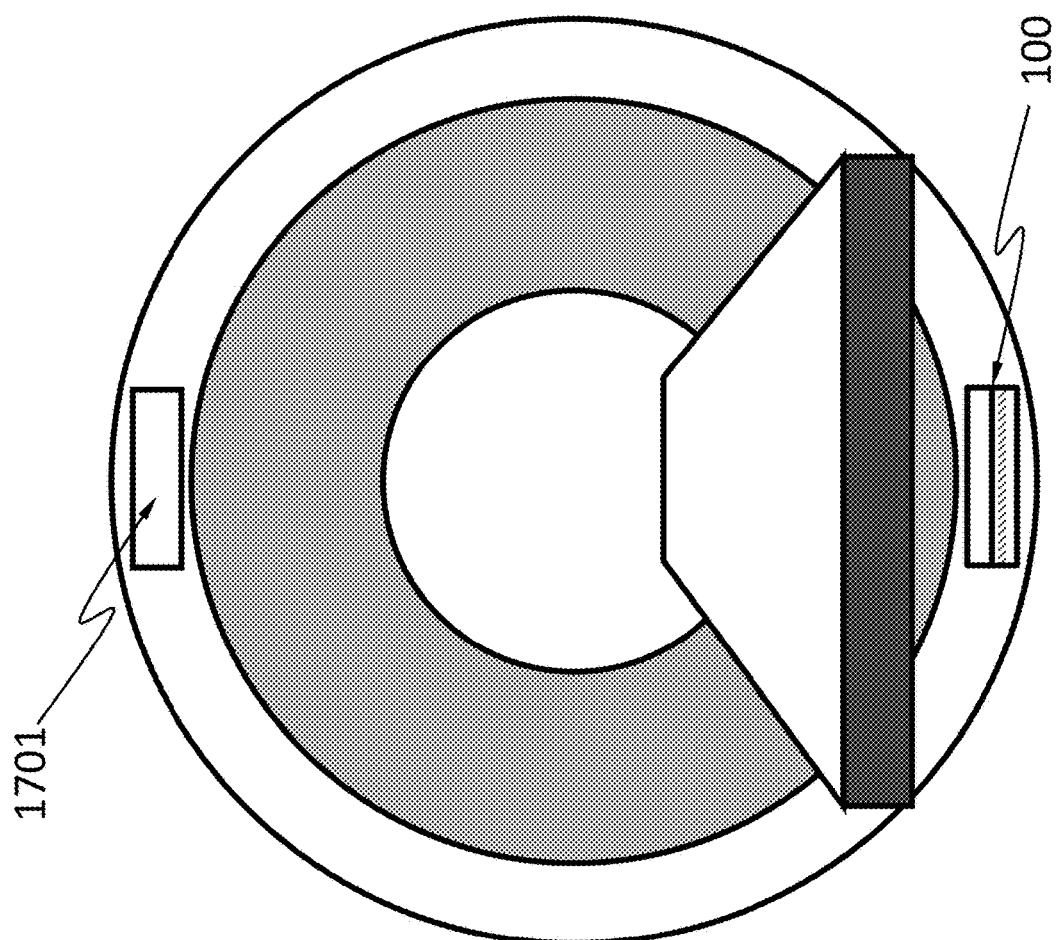

RADIATION DETECTOR SUITABLE FOR A PULSED RADIATION SOURCE

TECHNICAL FIELD

The disclosure herein relates to a radiation detector suitable for a pulsed radiation source.

BACKGROUND

A radiation detector is a device that measures a property of a radiation. Examples of the property may include a spatial distribution of the intensity, phase, and polarization of the radiation. The radiation may be one that has interacted with a subject. For example, the radiation measured by the radiation detector may be a radiation that has penetrated or reflected from the subject. The radiation may be an electromagnetic radiation such as infrared light, visible light, ultraviolet light, X-ray or γ-ray. The radiation may be of other types such as α-rays and β-rays.

One type of radiation detectors is based on interaction between the radiation and a semiconductor. For example, a radiation detector of this type may have a semiconductor layer that absorbs the radiation and generate charge carriers (e.g., electrons and holes) and circuitry for detecting the charge carriers.

Radiation detectors may be negatively impacted by "dark" noise (e.g., dark current). Dark noise in a radiation detector includes physical effects present even if no radiation the radiation detector is configured to detect is incident on the radiation detector. Isolating or reducing the impact of the dark noise to the overall signals detected by the radiation detector is helpful to make the radiation detector more useful.

SUMMARY

Disclosed herein is a radiation detector, comprising: a plurality of pixels, and a controller; wherein each pixel is configured to detect radiation emitted from a pulsed radiation source; wherein the pulsed radiation source is configured to emit radiation during a plurality of ON periods and configured not to emit radiation during a plurality of OFF periods; wherein the controller is configured to determine that the pulsed radiation source is at one of the ON periods or at one of the OFF periods; wherein the controller is configured to cause the pixels to integrate signals or not to integrate signals with determination that the radiation source is at one of the ON periods or at one of the OFF periods.

According to an embodiment, the radiation is X-ray.

According to an embodiment, the signals during the ON periods comprise signals attributable to radiation from the pulsed radiation source and signals attributable to dark noise.

According to an embodiment, the signals during the OFF periods comprise signals attributable to dark noise but not signals attributable to radiation from the pulsed radiation source.

According to an embodiment, the controller is configured to cause the pixels to integrate signals during all of the ON periods.

According to an embodiment, the controller is configured to cause the pixels not to integrate signals during at least some of the OFF periods.

According to an embodiment, the controller is configured to cause the pixels not to integrate signals during all of the OFF periods.

According to an embodiment, the controller is configured to process, during one of the OFF periods, signals of the pixels integrated.

According to an embodiment, the controller is configured to digitize, during one of the OFF periods, signals of the pixels integrated.

According to an embodiment, the controller is configured to reset, during one of the OFF periods, signals of the pixels integrated.

According to an embodiment, the radiation detector and the pulsed radiation source are synchronized to a same clock.

According to an embodiment, the controller configured to determine that the pulsed radiation source is at one of the ON periods or at one of the OFF periods based on a clock signal from the clock.

According to an embodiment, the radiation detector comprises a device configured to detect an intensity of the radiation from the pulsed radiation source as a function of time.

According to an embodiment, the device has a lower shot noise than the pixels.

According to an embodiment, the controller configured to determine that the pulsed radiation source is at one of the ON periods or at one of the OFF periods based on the intensity of the radiation.

According to an embodiment, the controller is configured to determine that the pulsed radiation source is at one of the ON periods or at one of the OFF periods, using the pixels.

According to an embodiment, the controller is configured to determine that the pulsed radiation source is at one of the ON periods or at one of the OFF periods, based on a combined signal of a plurality of the pixels.

According to an embodiment, exposure of the pixels to the radiation is synchronized.

Disclosed herein is a radiation detector: wherein the radiation detector is configured to detect radiation from a pulsed radiation source; wherein the pulsed radiation source is configured to emit radiation during a plurality of ON periods and configured not to emit radiation during a plurality of OFF periods; wherein the radiation detector is configured to integrate signals during at least some of the ON periods and configured not to integrate signals during at least some of the OFF periods.

According to an embodiment, the radiation is X-ray.

According to an embodiment, the ON periods and the OFF periods have adjustable lengths.

According to an embodiment, the signals during the ON periods comprise signals attributable to radiation from the pulsed radiation source and signals attributable to dark noise.

According to an embodiment, the signals during the OFF periods comprise signals attributable to dark noise but not signals attributable to radiation from the pulsed radiation source.

According to an embodiment, the radiation detector is configured to determine that the pulsed radiation source is at one of the ON periods or at one of the OFF periods.

According to an embodiment, the radiation detector is configured to determine whether to integrate the signals based on determination that the radiation source is at one of the ON periods or at one of the OFF periods.

Disclosed herein is a system comprising any one of the radiation detectors above, wherein the system is configured to perform X-ray radiography on human chest or abdomen.

Disclosed herein is a system comprising any one of the radiation detectors above, wherein the system is configured to perform X-ray radiography on human mouth.

Disclosed herein is a cargo scanning or non-intrusive inspection (NII) system, comprising any one of the radiation detectors above and the pulsed radiation source, wherein the cargo scanning or non-intrusive inspection (NII) system is configured to form an image using backscattered radiation.

Disclosed herein is a cargo scanning or non-intrusive inspection (NII) system, comprising any one of the radiation detectors above and the pulsed radiation source, wherein the cargo scanning or non-intrusive inspection (NII) system is configured to form an image using radiation transmitted through an object inspected.

Disclosed herein is a full-body scanner system comprising any one of the radiation detectors above and the pulsed radiation source.

Disclosed herein is an X-ray computed tomography (X-ray CT) system comprising any one of the radiation detectors above and the pulsed radiation source, wherein the pulsed radiation source emits X-ray.

BRIEF DESCRIPTION OF FIGURES

FIG. 2 schematically shows the radiation intensity output from the pulsed radiation source as a function of time.

FIG. 3A schematically shows the radiation output from a pulsed radiation source as a function of time, where the pulsed radiation source has a duty cycle of 50%.

FIG. 3B schematically shows that a radiation detector may continuously integrate signals across all ON periods and all OFF periods of the pulsed radiation source shown in FIG. 3A.

FIG. 3C schematically shows the signals attributable to the dark noise and the signals attributable to the radiation from the pulsed radiation source shown in FIG. 3A, during signals integration shown in FIG. 3B.

FIG. 3D schematically shows only the portion attributable to the dark noise in the signals of the radiation detector (or its pixels) of FIG. 3A, FIG. 3B and FIG. 3C integrated.

FIG. 4A schematically shows the radiation output from a pulsed radiation source as a function of time, where the pulsed radiation source has a duty cycle of 75%.

FIG. 4B schematically shows that a radiation detector may continuously integrate signals across all ON periods and all OFF periods of the pulsed radiation source shown in FIG. 4A.

FIG. 4C schematically shows the signals attributable to the dark noise and the signals attributable to the radiation from the pulsed radiation source shown in FIG. 4A, during signals integration shown in FIG. 4B.

FIG. 4D schematically shows only the portion attributable to the dark noise in the signals of the radiation detector (or its pixels) of FIG. 4A, FIG. 4B and FIG. 4C integrated.

FIG. 5A schematically shows the radiation output from a pulsed radiation source as a function of time, where the pulsed radiation source has a duty cycle of 50%.

FIG. 5B schematically shows that a radiation detector may continuously integrate signals across all ON periods and some OFF periods but not across the other OFF periods of the pulsed radiation source shown in FIG. 5A.

FIG. 5C schematically shows the signals attributable to the dark noise and the signals attributable to the radiation from the pulsed radiation source shown in FIG. 5A, during signals integration shown in FIG. 5B.

FIG. 5D schematically shows only the portion attributable to the dark noise in the signals of the radiation detector (or its pixels) of FIG. 5A, FIG. 5B and FIG. 5C integrated.

FIG. 6A schematically shows the radiation output from a pulsed radiation source as a function of time, where the pulsed radiation source has a duty cycle of 50%.

FIG. 6B schematically shows that a radiation detector may continuously integrate signals across all ON periods but across none of the OFF periods of the pulsed radiation source shown in FIG. 6A.

FIG. 9A schematically shows an embodiment where the radiation detector and the pulsed radiation source are synchronized to the same clock.

FIG. 9B schematically shows an embodiment where the radiation detector has a device configured to detect which period the pulsed radiation source is at.

FIG. 9C schematically shows an embodiment where the radiation detector uses some or all of it pixels to detect which period the pulsed radiation source is at.

FIG. 12-FIG. 17 each schematically show a system comprising the radiation detector described herein.

DETAILED DESCRIPTION

Figure 1:
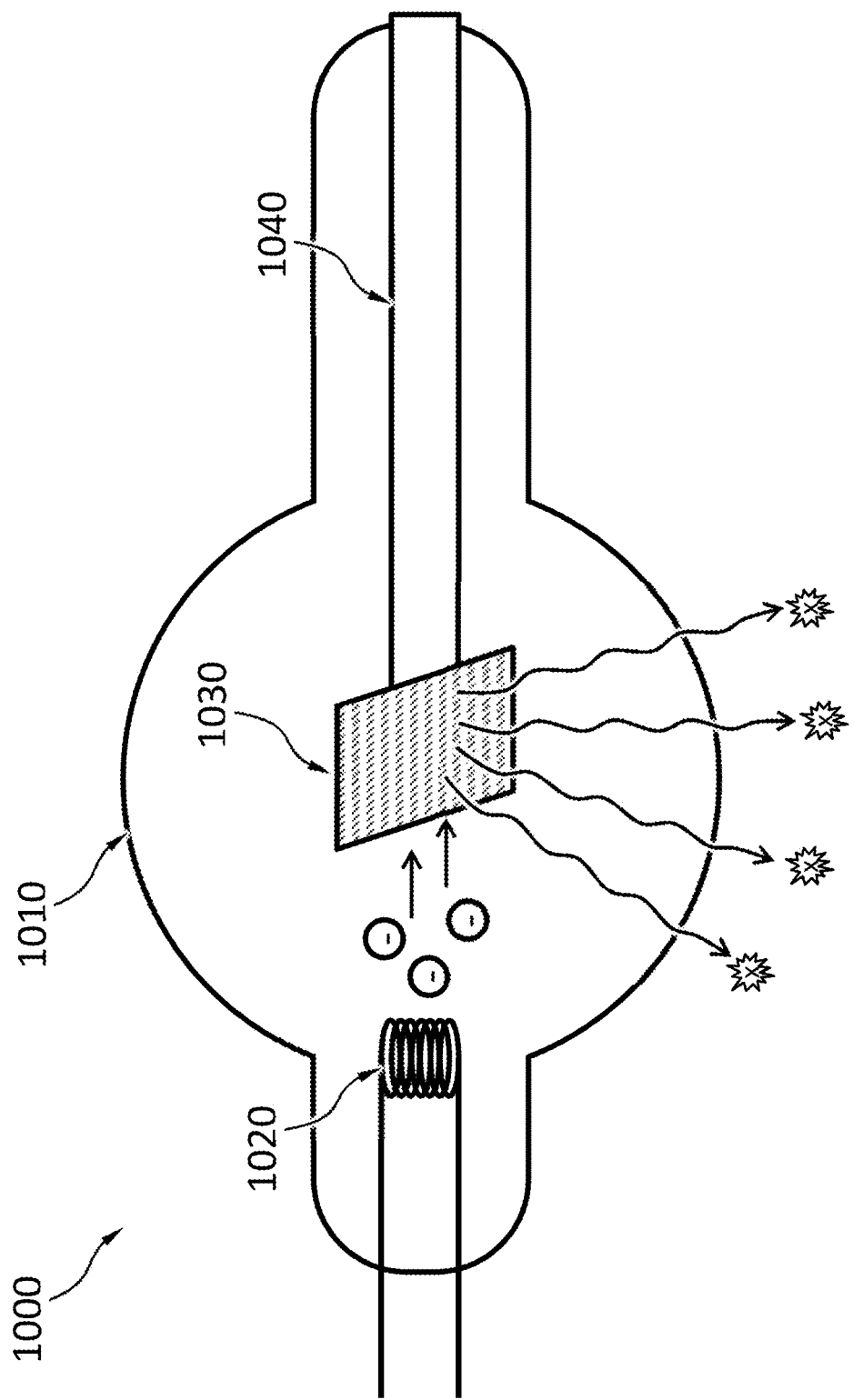
FIG. 1 schematically shows an X-ray tube as an example of a pulsed radiation source.

FIG. 1 schematically shows an X-ray tube 1000 as an example of a pulsed radiation source. The radiation detectors disclosed herein may be used with other pulsed radiation sources. The X-ray tube 1000 has a vacuum tube 1010, a cathode 1020 and anode 1030 housed in the vacuum tube 1010. The cathode 1020 is configured to emit electrons. For example, the cathode 1020 may be a filament of a metal (e.g., tungsten) of high melting point and the emission of the electrons from the filament may be caused by the thermionic effect. A high voltage (e.g., 30 kV to 150 kV) between the cathode 1020 and the anode 1030 establishes an electric field, which accelerates the emitted electrons toward the anode 1030. Examples of the material of the anode 1030 may include tungsten, molybdenum and copper. When the electrons hit the anode 1030, X-ray is emitted from the anode 1030. The emitted X-ray may include a portion having a smooth intensity variation with the wavelength and a portion having several sharp peaks. The first portion is due to deceleration of the electrons (the bremsstrahlung effect) in the anode 1030. The second portion is due to relaxation of electrons at an outer shell of the atoms of the anode 1030 to a lower shell. The X-ray tube 1000 may have a heat sink 1040 thermally connected to the anode 1030.

A pulsed radiation source may emit radiation in pulses. Namely, during operation, the pulsed radiation source emits radiation for a period of time ("ON period") and does not emit radiation for another period of time ("OFF period"). In the example of the X-ray tube here, the pulses of radiation may be caused by pulsing the flow of the electrons from the cathode 1020 to the anode 1030. Namely, the flow of the electrons toward the anode 1030 may be on during an ON period and then may be off during an OFF period. The lengths of the ON periods and the OFF periods may be adjustable, for example, by a switch mode power supply.

A switch mode power supply transfers electrical power from a power source (AC or DC) to a load (e.g., the electric field between the anode and cathode of an X-ray tube) using a switching regulator. The switching regulator rapidly switches power to the load on and off. The duty cycle of the switch determines how much power is transferred to the load. The switch regulator has very little power dissipation and thus is very efficient. In contrast, a linear regulator provides the desired output voltage by dissipating excess power in Ohmic losses (i.e., as heat). The switch mode power supply may be able to generate output voltages which are higher than the input, or of opposite polarity.

FIG. 2 schematically shows the intensity of the radiation emitted by the pulsed radiation source as a function of time. The intensity during ON periods 2010 is non-zero and may be substantially constant. The intensity during the OFF periods 2020 may be substantially zero.

FIG. 3B schematically shows that a radiation detector may continuously integrate signals across all ON periods 3010 and all OFF periods 3020 of a pulsed radiation source as shown in FIG. 3A, where the pulsed radiation source has a duty cycle of 50%. The duty cycle of the pulsed radiation source is the ratio of the ON period over the sum of the ON period and the OFF period. Signals attributable to the radiation from the pulsed radiation source are present during the ON periods 3010 but not during the OFF periods 3020. Signals attributable to the dark noise are present during both the ON periods 3010 and the OFF periods 3020. Therefore, during the ON periods 3010, both signals are present; and during the OFF periods 3020, the signals attributable to the dark noise are present but the signals attributable to the radiation from the pulsed radiation source are not present.

FIG. 3C schematically shows the signals attributable to the dark noise and the signals attributable to the radiation from the pulsed radiation source with 50% duty cycle shown in FIG. 3A, during signals integration shown in FIG. 3B. Within each ON period 3010 or OFF period 3020, the height 3030H of a dotted box 3030 shows the magnitude of the total signals integrated during that period 3010 or 3020; the height 3030D of a shaded portion of the dotted box 3030 shows the magnitude of the signals attributable to the dark noise during that period 3010 or 3020. The labels "ON" below the dotted boxes 3030 indicate that the radiation detector (or its pixels) integrates signals during the periods the dotted boxes are associated with, respectively. The signals 3040 the radiation detector (or its pixels) integrates during the four ON periods 3010 and the three OFF periods 3020 shown in FIG. 3C include a portion 3040R attributable to the radiation from the pulsed radiation source and a portion 3040D attributable to the dark noise. FIG. 3C shows that during the OFF periods 3020, the signals attributable to the dark noise are still being integrated by the radiation detector (or its pixels), despite that there are substantially zero signals attributable to the radiation from the pulsed radiation source. FIG. 3D shows only the portion 3040D attributable to the dark noise. During the OFF periods 3020, the radiation detector only integrates the signals attributable to the dark noise, but not the signals attributable to the radiation. Therefore, if the OFF periods are reduced relative to the ON periods, i.e., if the duty cycle of the pulsed radiation source is increased, the proportion of the portion 3040D attributable to the dark noise relative to the signals 3040 can be reduced.

FIG. 4B schematically shows that a radiation detector may continuously integrate signals across all ON periods 4010 and all OFF periods 4020 of a pulsed radiation source as shown in FIG. 4A, where the pulsed radiation source has a duty cycle of 75% and a period (i.e., the sum of an ON period and an OFF period) identical to the pulsed radiation source in FIG. 3A. Signals attributable to the radiation from the pulsed radiation source are present during the ON periods 4010 but not during the OFF periods 4020. Signals attributable to the dark noise are present during both the ON periods 4010 and the OFF periods 4020. Therefore, during the ON periods 4010, both signals are present; and during the OFF periods 4020, the signals attributable to the dark noise are present but the signals attributable to the radiation from the pulsed radiation source are not present. Compared to the pulsed radiation source as shown in FIG. 3A, the portion attributable to the radiation is larger because the ON periods are longer.

FIG. 4C schematically shows the signals attributable to the dark noise and the signals attributable to the radiation from the pulsed radiation source with 75% duty cycle shown in FIG. 4A, during signals integration shown in FIG. 4B. Within each ON period 4010 or OFF period 4020, the height 4030H of a dotted box 4030 shows the magnitude of the total signals integrated during that period 4010 or 4020; the height 4030D of a shaded portion of the dotted box 4030 shows the magnitude of the signals attributable to the dark noise. The labels "ON" below the dotted boxes 4030 indicate that the radiation detector (or its pixels) integrates signals during the periods the dotted boxes are associated with, respectively. The signals 4040 the radiation detector (or its pixels) integrates during the four ON periods 4010 and the three OFF periods 4020 shown in FIG. 4C include a portion 4040R attributable to the radiation from the pulsed radiation source and a portion 4040D attributable to the dark noise. FIG. 4C shows that during the OFF periods 4020, the signals attributable to the dark noise are still being integrated by the radiation detector (or its pixels), despite that there are substantially zero signals attributable to the radiation from the pulsed radiation source. However, compared to the scenario shown in FIG. 3C, the OFF periods 4020 are shorter than the OFF periods 3020 and thus the magnitude to the signals attributable to the dark noise integrated during the OFF periods 4020 into the signals 4040 is smaller. FIG. 4D shows only the portion 4040D attributable to the dark noise. During the OFF periods 4020, the radiation detector only integrates the signal attributable to the dark noise, but not the signal attributable to the radiation. Therefore, if the radiation detector stops integrating signals during at least some of the OFF periods, the proportion of the portion 4040D attributable to the dark noise relative to the signals 4040 can be reduced.

FIG. 5B schematically shows that a radiation detector may integrate signals across all ON periods 5010 and some OFF periods 5021 but not across the other OFF periods 5020 of a pulsed radiation source as shown in FIG. 5A, where the pulsed radiation source has a duty cycle of 50% and a period (i.e., the sum of an ON period and an OFF period) identical to the pulsed radiation source in FIG. 3A. Signals attributable to the radiation from the pulsed radiation source are present during the ON periods 5010 but not during the OFF periods 5020 or 5021. Signals attributable to the dark noise are present during both the ON periods 5010 and the OFF periods 5020 and 5021. Therefore, during the ON periods 5010, both signals are present; and during the OFF periods 5020 and 5021, the signals attributable to the dark noise are present but the signals attributable to the radiation from the pulsed radiation source are not present. Compared to the pulsed radiation source as shown in FIG. 3A, the portion attributable to the radiation is the same but the portion attributable to the dark noise is smaller because the radiation detector does not integrate signals during at least some of the OFF periods.

FIG. 5C schematically shows the signals attributable to the dark noise and the signals attributable to the radiation from the pulsed radiation source with 50% duty cycle shown in FIG. 5A, during signals integration shown in FIG. 5B. Within each ON period 5010 or OFF period 5020 or 5021, the height 5030H of a dotted box 5030 shows the magnitude of the total signals integrated during that period 5010, 5020 or 5021; the height 5030D of a shaded portion of the dotted box 5030 shows the magnitude of the signals attributable to the dark noise. The labels "ON" below the dotted boxes 5030 indicate that the radiation detector (or its pixels) integrates signals during the periods the dotted boxes are associated with, respectively. The labels "OFF" below the dotted boxes 5030 indicate that the radiation detector does not integrate signals during the periods the dotted boxes are associated with, respectively. The signals 5040 the radiation detector (or its pixels) integrates during the four ON periods 5010 and the three OFF periods 5020 and 5021 shown in FIG. 5C include a portion 5040R attributable to the radiation from the pulsed radiation source and a portion 5040D attributable to the dark noise. FIG. 5C shows that during the OFF periods 5021, the signals attributable to the dark noise are still being integrated by the radiation detector (or its pixels), despite that there are substantially zero signals attributable to the radiation from the pulsed radiation source. FIG. 5C also shows that during the OFF periods 5020, the signals attributable to the dark noise are not being integrated into the signals 5040, and that all the signals attributable to the radiation from the pulsed radiation source are integrated into the signals 5040. FIG. 5D shows only the portion 5040D attributable to the dark noise. During the OFF periods 5021, the radiation detector only integrates the signal attributable to the dark noise, but not the signal attributable to the radiation. Therefore, if the radiation detector stops integrating signals during all of the OFF periods, the proportion of the portion 5040D attributable to the dark noise relative to the signals 5040 can be reduced.

FIG. 6B schematically shows that a radiation detector may integrate signals across all ON periods 6010 but across none of the OFF periods 6020 of a pulsed radiation source as shown in FIG. 6A, where the pulsed radiation source has a duty cycle of 50% and a period (i.e., the sum of an ON period and an OFF period) identical to the pulsed radiation source in FIG. 3A. Signals attributable to the radiation from the pulsed radiation source are present during the ON periods 6010 but not during the OFF periods 6020. Signals attributable to the dark noise are present during both the ON periods 6010 and the OFF periods 6020. Therefore, during the ON periods 6010, both signals are present; and during the OFF periods 6020, the signals attributable to the dark noise are present but the signals attributable to the radiation from the pulsed radiation source are not present. Compared to the pulsed radiation source as shown in FIG. 3A, the portion attributable to the radiation is the same but the portion attributable to the dark noise is smaller because the radiation detector does not integrate signals during any of the OFF periods.

Figures 6C, 6D:
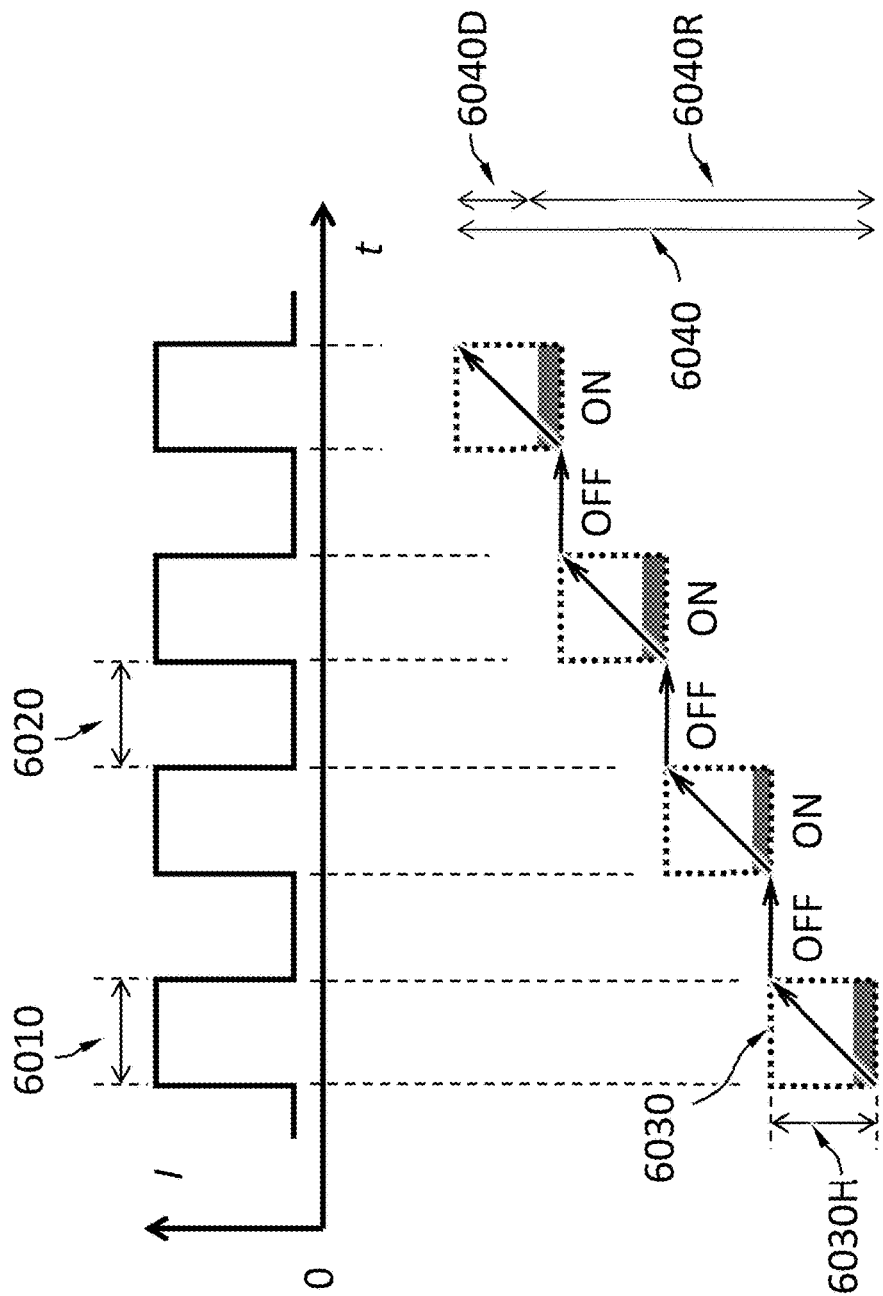
FIG. 6C schematically shows the signals attributable to the dark noise and the signals attributable to the radiation from the pulsed radiation source shown in FIG. 6A, during signals integration shown in FIG. 6B.
FIG. 6D schematically shows only the portion attributable to the dark noise in the signals of the radiation detector (or its pixels) of FIG. 6A, FIG. 6B and FIG. 6C integrated.

FIG. 6C schematically shows the signals attributable to the dark noise and the signals attributable to the radiation from the pulsed radiation source with 50% duty cycle shown in FIG. 6A, during signals integration shown in FIG. 6B. Within each ON period 6010 or OFF period 6020, the height 6030H of a dotted box 6030 shows the magnitude of the total signals integrated during that period 6010 or 6020; the height 6030D of a shaded portion of the dotted box 6030 shows the magnitude of the signals attributable to the dark noise. The labels "ON" below the dotted boxes 6030 indicate that the radiation detector (or its pixels) integrates signals during the periods the dotted boxes are associated with, respectively. The labels "OFF" below the dotted boxes 6030 indicate that the radiation detector does not integrate signals during the periods the dotted boxes are associated with, respectively. The signals 6040 the radiation detector (or its pixels) integrates during the four ON periods 6010 and the three OFF periods 6020 shown in FIG. 6C include a portion 6040R attributable to the radiation from the pulsed radiation source and a portion 6040D attributable to the dark noise. FIG. 6C shows that during all of the OFF periods 6020, the signals attributable to the dark noise are not being integrated into the signals 6040, and that all the signals attributable to the radiation from the pulsed radiation source are integrated into the signals 6040. FIG. 6D shows only the portion 6040D attributable to the dark noise.

The impact of the dark noise in a radiation detector may not be proportion to the radiation intensity the radiation detector receives during the ON periods from the radiation source. The impact of the dark noise may be unrelated to the intensity. For example, the impact of the dark noise may be affected by the temperature or bias voltages of the radiation detector, but not to the intensity of the radiation. Increasing the intensity thus may relatively decrease the impact of the dark noise.

Figure 7B:
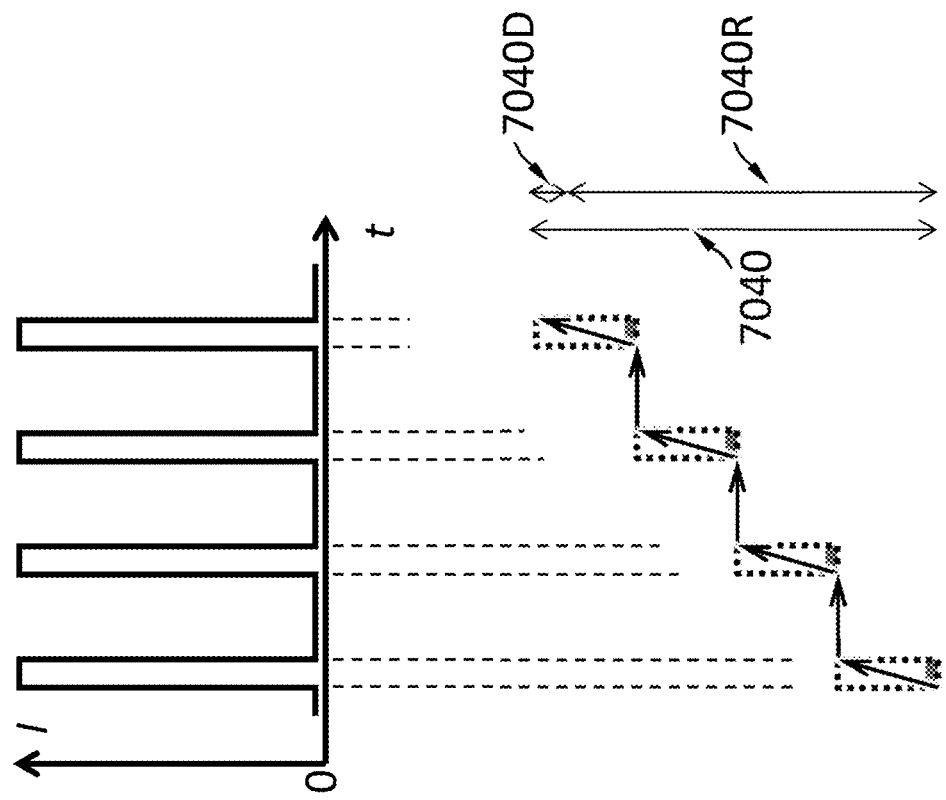
FIG. 7A and FIG. 7B show a comparison on the signals of the same radiation detector obtained from two different pulsed radiation sources, respectively.
Figure 7A:
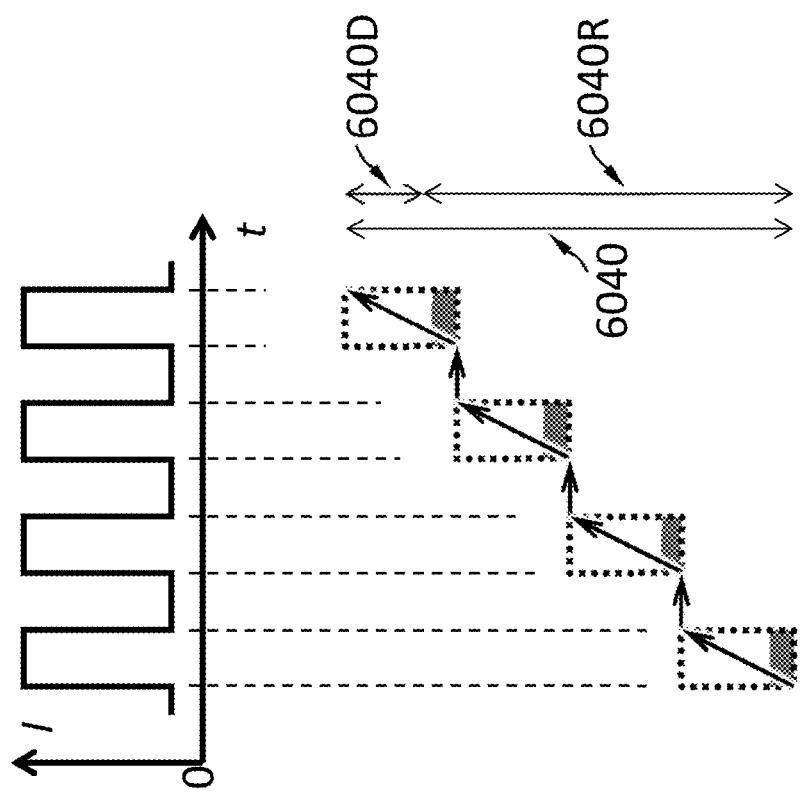

FIG. 7A and FIG. 7B show a comparison on the signals of the same radiation detector obtained from two different pulsed radiation sources, respectively. The signals in FIG. 7A are obtained from the pulsed radiation source shown in FIG. 6C, which has a 50% duty cycle. The signals in FIG. 7B are obtained from a pulsed radiation source that has a 25% duty cycle and twice the intensity of the pulsed radiation source shown in FIG. 7A. The temporal average intensities of these two pulsed radiation sources are the same. The signals 7040 the radiation detector (or its pixels) integrates during the four ON periods and the three OFF periods shown in FIG. 7B include a portion 7040R attributable to the radiation from the pulsed radiation source and a portion 7040D attributable to the dark noise. The portion 7040D is not affected by the intensity and is proportional to the length of the ON periods. Therefore, the portion 7040D is only half of the portion 6040D because the length of the ON periods of the pulsed radiation source in FIG. 7B is half of the length of the ON periods of the pulsed radiation source in FIG. 7A. The portion 7040R is affected by both the intensity and the length of the ON periods. In this example, the portion 7040R is proportional to the intensity and the length of the ON periods. Therefore, the portion 7040R is the same as the portion 6040R because the length of the ON periods of the pulsed radiation source in FIG. 7B is half of the length of the ON periods of the pulsed radiation source in FIG. 7A but the intensity of the pulsed radiation source in FIG. 7B is twice the intensity of the pulsed radiation source in FIG. 7A. Therefore, the portion 7040D is relatively smaller in the signal 7040 than the portion 6040D in the signal 6040.

Figure 8:
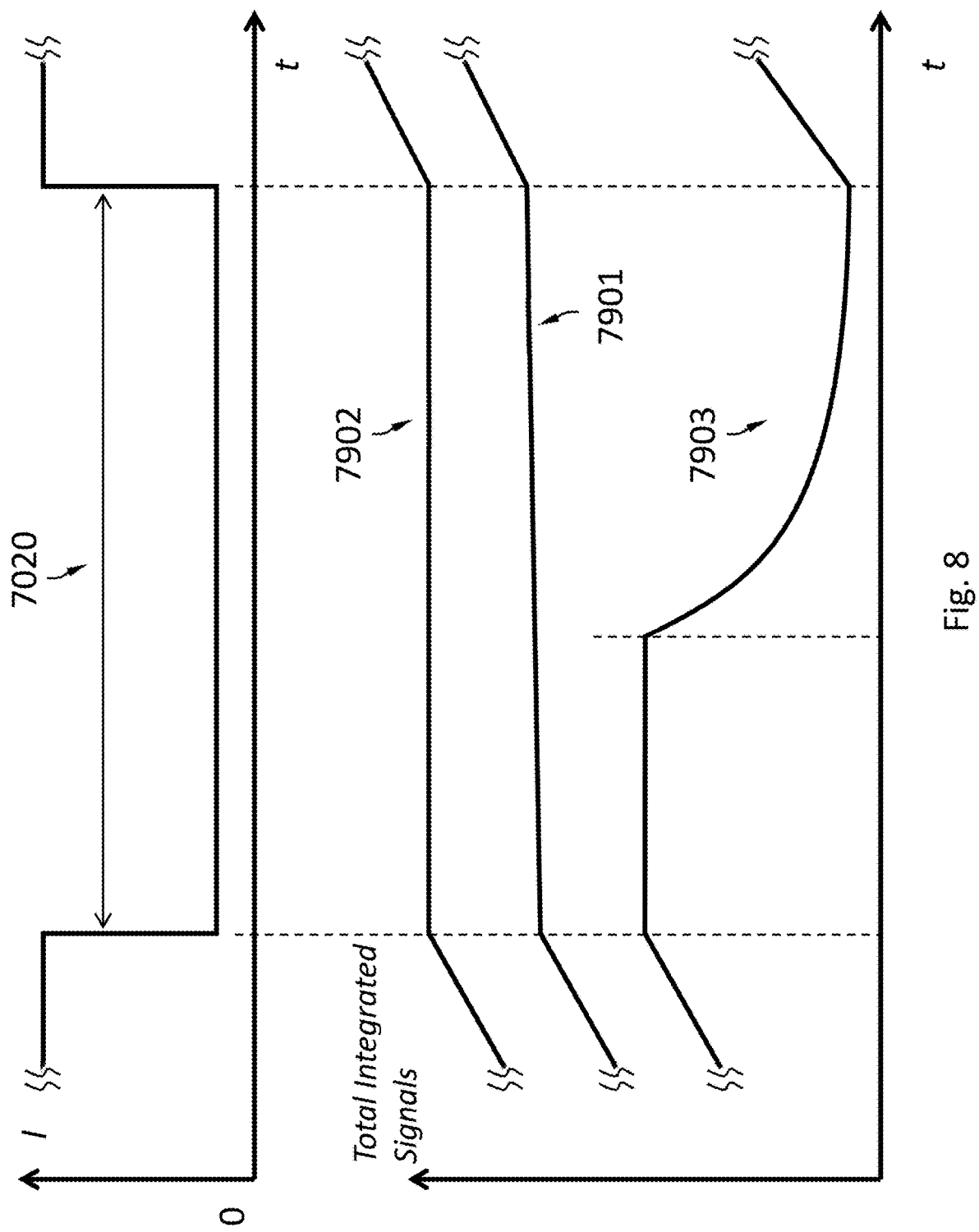
FIG. 8 schematically shows the signals of the radiation detector (or its pixels) integrated maybe processed in an OFF period of the pulsed radiation source.

The radiation detector may have a variety of operations during an OFF period 7020. In an example, as shown in FIG. 8, the radiation detector may continue integrating the signals attributable to the dark noise during the OFF period 7020 and the signals 7901 the radiation detector (or its pixels) integrates as a function of time may have a slight increase during the OFF period 7020. In an example, as shown in FIG. 6C, the radiation detector may cease to integrate the signals during the OFF period 7020 and the signals 7902 the radiation detector (or its pixels) integrates as a function of time may have no increase during the OFF period 7020. In another example, the radiation detector may cease to integrate the signals during the OFF period 7020, process (e.g., digitize and transmit), during the OFF period 7020, the signals 7903 the radiation detector (or its pixels) integrated, and reset the signals 7903. The signals 7903 may have no increase during the OFF period 7020 before the reset and relax to zero. For example, if the radiation detector collects charge carriers generated in an absorption layer by incident photons and stores the charge carriers on a capacitor, the voltage across the capacitor may be measured and the capacitor discharged during the OFF period 7020.

The exposure of the pixels of the radiation detector may be synchronized. Synchronizing exposure of the pixels is sometimes referred to as "global shuttering." Synchronization of the exposure of the pixels does not necessarily require that the pixels are configured to physically receive radiation during the same period of time; instead, synchronization means that the signals of the pixels are attributable to radiation of the same period of time. For example, Pixel A and Pixel B are still synchronized if Pixel A is configured to physically receive radiation between to and $(t_0+2t_1)$, Pixel B is configured to physically receive radiation between $(t_0+t_1)$ and $(t_0+3t_1)$, and the signals of Pixel A and Pixel B are attributable to the radiation they receive between $(t_0+t_1)$ and $(t_0+2t_1)$.

As shown above, the radiation detector may control whether it integrates signals at a given time based on which period (i.e., an ON period or an OFF period) the pulsed radiation source is at. FIG. 9A schematically shows an embodiment where the radiation detector 8020 and the pulsed radiation source 8010 are synchronized to the same clock 8030. The clock signal from the clock 8030 may be used to determine the lengths of the ON period and the OFF period of the pulsed radiation source 8010. In an X-ray tube as an example of the pulsed radiation source 8010, the clock signal from the clock 8030 may be used to determine the temporal characteristics of the electric field 8011 between the anode and the cathode of the X-ray tube. The clock signal from the clock 8030 is also fed into a controller 8021 of the radiation detector 8020. The controller 8021 may use the clock signal to determine that the pulsed radiation source 8010 is at an ON period or an OFF period, and to determine when signals integration at the pixels 8022 of the radiation detector 8020 should occur. The controller 8021 may have a processor and a memory with instructions stored therein, and executing the instructions causes the controller 8021 to perform its functions.

Figure 9B:
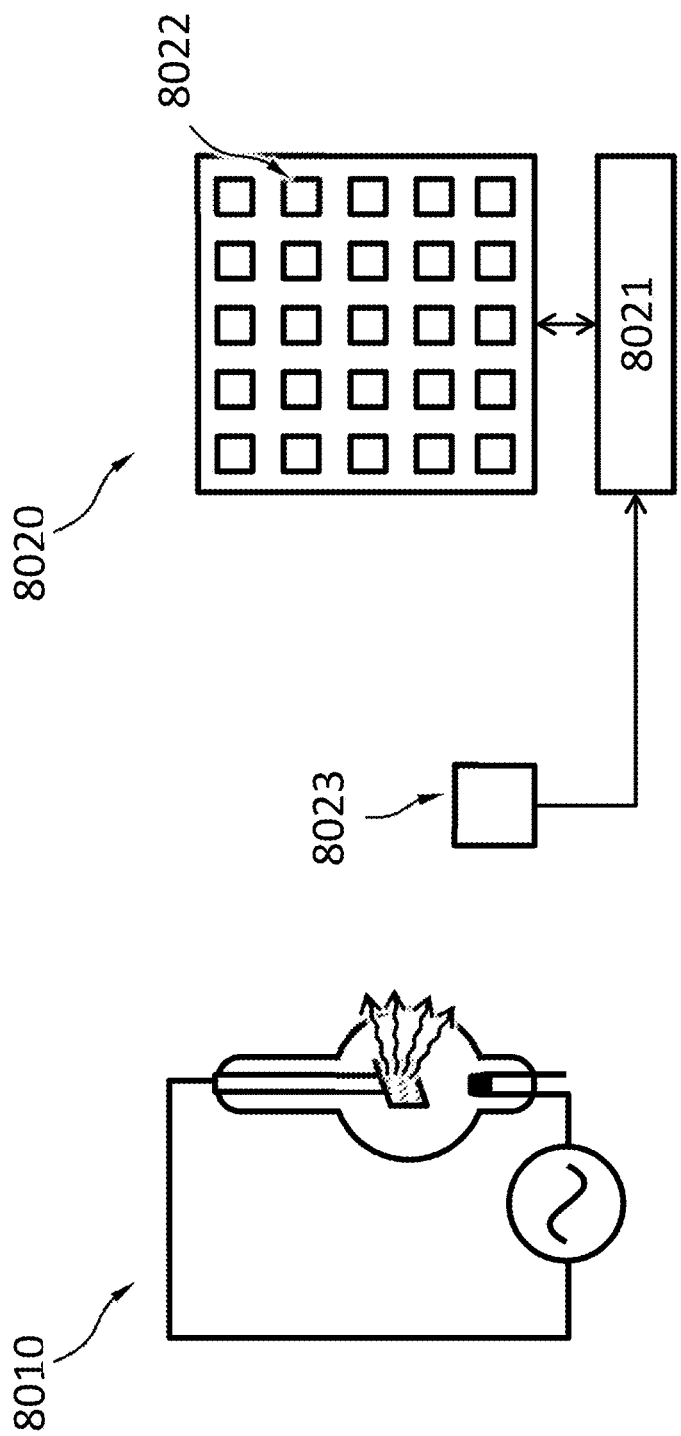

FIG. 9B schematically shows an embodiment where the radiation detector 8020 has a device 8023 configured to detect which period (i.e., an ON period or an OFF period) the pulsed radiation source 8010 is at. Therefore, there is no need to synchronize the pulsed radiation source 8010 and the radiation detector 8020 to the same clock. The device 8023 may detect the intensity of the radiation from the pulsed radiation source 8010 as a function of time. The device may have lower shot noise than the pixels, e.g., by having a larger area than the pixels 8022 of the radiation detector 8020, or by being placed closer to the pulsed radiation source 8010 than the pixels 8022. The device 8023 may lack spatial resolution. The intensity of the radiation detected by the device 8023 may be sent to the controller 8021. The controller 8021 can use the intensity of the radiation detected by the device 8023 to determine that the pulsed radiation source 8010 is at an ON period or an OFF period, and to determine when signals integration at the pixels 8022 of the radiation detector 8020 should occur. The device 8023 may continuously detect the intensity of the radiation or do so at a series of time points.

FIG. 9C schematically shows an embodiment where the radiation detector 8020 uses some or all of it pixels 8022 to detect which period the pulsed radiation source 8010 is at. Therefore, there is no need to have the device 8023 or to synchronize the pulsed radiation source 8010 and the radiation detector 8020 to the same clock. In order to reduce the shot noise, the signals of a plurality of the pixels 8022 may be combined. The combined signals represent the intensity of the radiation from the pulsed radiation source 8010 as a function of time. The intensity of the radiation detected by the pixels 8022 may be fed into the controller 8021. The controller 8021 can use the intensity of the radiation to determine that the timing of the ON period and OFF period of the pulsed radiation source 8010, and to determine when signals integration at the pixels 8022 of the radiation detector 8020 should occur. The detection of the period of the pulsed radiation source 8010 may occur at a calibration phase, before a subject is imaged using the radiation source 8010 and the radiation detector 8020.

Figure 10:
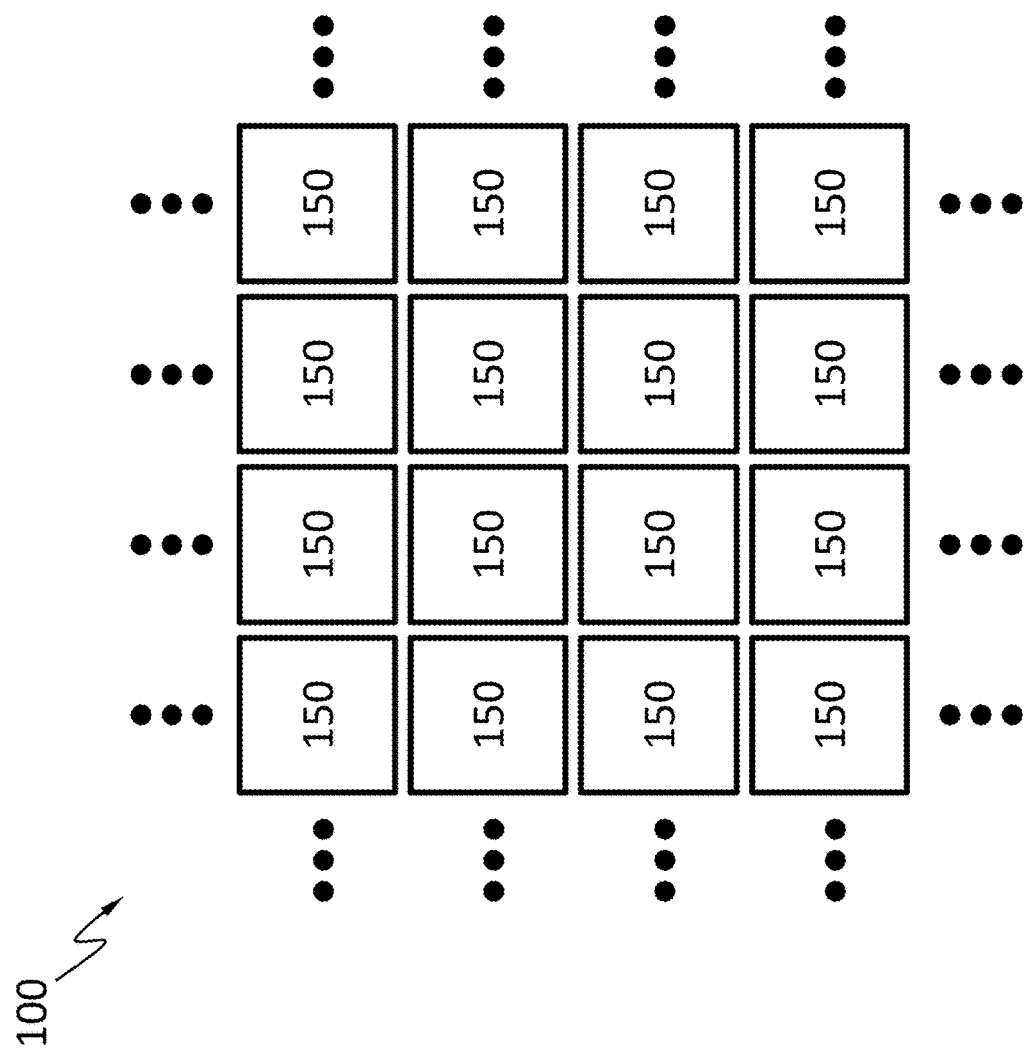
FIG. 10 schematically shows a radiation detector suitable for a pulsed radiation source.

FIG. 10 schematically shows a radiation detector 100 suitable for a pulsed radiation source, according to an embodiment. The radiation detector 100 has an array of pixels 150. The array may be a rectangular array, a honeycomb array, a hexagonal array or any other suitable array. Each pixel 150 is configured to detect radiation from the pulsed radiation source incident thereon and may be configured measure a characteristic (e.g., the energy of the particles, the wavelength, the frequency) of the radiation. For example, each pixel 150 is configured to count numbers of photons incident thereon whose energy falls in a plurality of bins, within a period of time. All the pixels 150 may be configured to count the numbers of photons incident thereon within a plurality of bins of energy within the same period of time. Each pixel 150 may have its own analog-to-digital converter (ADC) configured to digitize an analog signal representing the energy of an incident photon into a digital signal. The pixels 150 may be configured to operate in parallel. For example, when one pixel 150 measures an incident photon, another pixel 150 may be waiting for a photon to arrive. The pixels 150 may not have to be individually addressable.

Figure 11A:
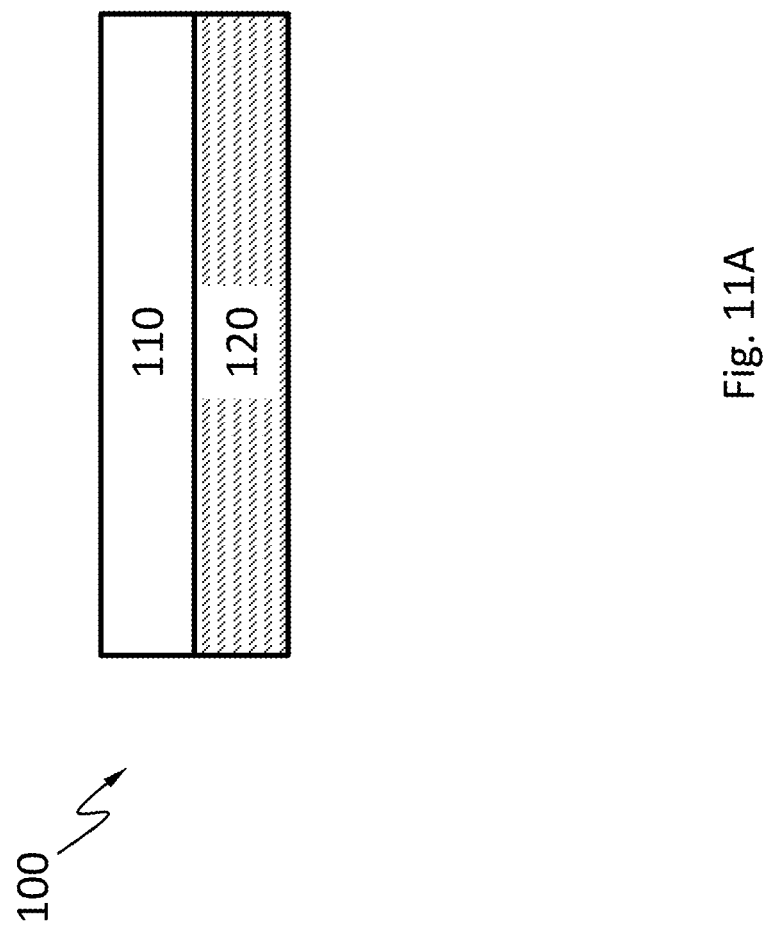
FIG. 11A schematically shows a cross-sectional view of the radiation detector.

FIG. 11A schematically shows a cross-sectional view of the radiation detector 100, according to an embodiment. The radiation detector 100 may include a radiation absorption layer 110 and an electronics layer 120 (e.g., an ASIC) for processing or analyzing electrical signals incident radiation generates in the radiation absorption layer 110. In an embodiment, the detector 100 does not comprise a scintillator. The radiation absorption layer 110 may include a semiconductor material such as, silicon, germanium, GaAs, CdTe, CdZnTe, or a combination thereof. The semiconductor may have a high mass attenuation coefficient for the radiation of interest.

Figure 11B:
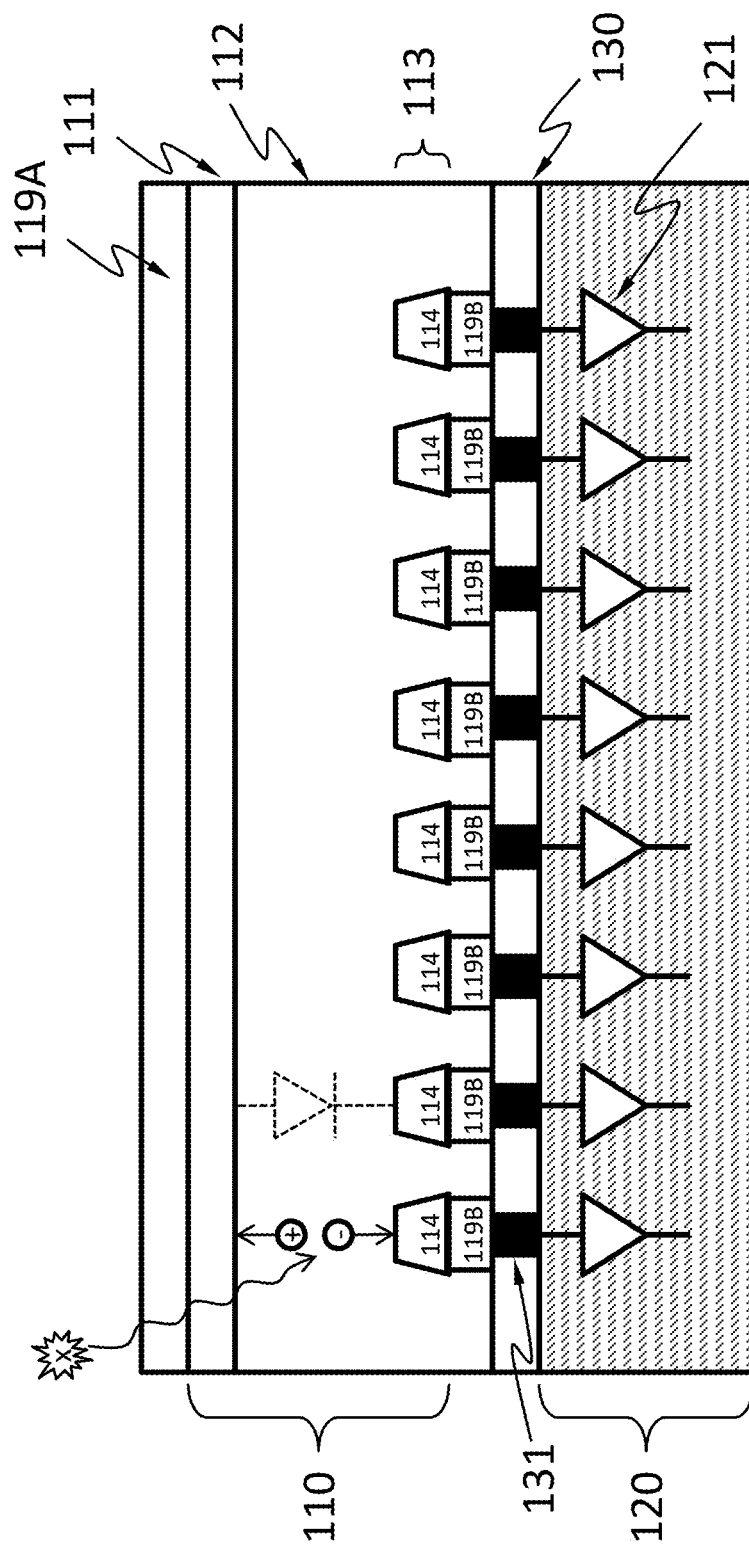
FIG. 11B schematically shows a detailed cross-sectional view of the radiation detector.

As shown in a detailed cross-sectional view of the radiation detector 100 in FIG. 11B, according to an embodiment, the radiation absorption layer 110 may include one or more diodes (e.g., p-i-n or p-n) formed by a first doped region 111, one or more discrete regions 114 of a second doped region 113. The second doped region 113 may be separated from the first doped region 111 by an optional the intrinsic region 112. The discrete portions 114 are separated from one another by the first doped region 111 or the intrinsic region 112. The first doped region 111 and the second doped region 113 have opposite types of doping (e.g., region 111 is p-type and region 113 is n-type, or region 111 is n-type and region 113 is p-type). In the example in FIG. 11B, each of the discrete regions 114 of the second doped region 113 forms a diode with the first doped region 111 and the optional intrinsic region 112. Namely, in the example in FIG. 11B, the radiation absorption layer 110 has a plurality of diodes having the first doped region 111 as a shared electrode. The first doped region 111 may also have discrete portions.

When radiation from the pulsed radiation source hits the radiation absorption layer 110 including diodes, the radiation photon may be absorbed and generate one or more charge carriers by a number of mechanisms. The charge carriers may drift to the electrodes of one of the diodes under an electric field. The field may be an external electric field. The electrical contact 119B may include discrete portions each of which is in electrical contact with the discrete regions 114. In an embodiment, the charge carriers may drift in directions such that the charge carriers generated by a single particle of the radiation are not substantially shared by two different discrete regions 114 ("not substantially shared" here means less than 2%, less than 0.5%, less than 0.1%, or less than 0.01% of these charge carriers flow to a different one of the discrete regions 114 than the rest of the charge carriers). Charge carriers generated by a particle of the radiation incident around the footprint of one of these discrete regions 114 are not substantially shared with another of these discrete regions 114. A pixel 150 associated with a discrete region 114 may be an area around the discrete region 114 in which substantially all (more than 98%, more than 99.5%, more than 99.9%, or more than 99.99% of) charge carriers generated by a particle of the radiation incident therein flow to the discrete region 114. Namely, less than 2%, less than 1%, less than 0.1%, or less than 0.01% of these charge carriers flow beyond the pixel.

Figure 11C:
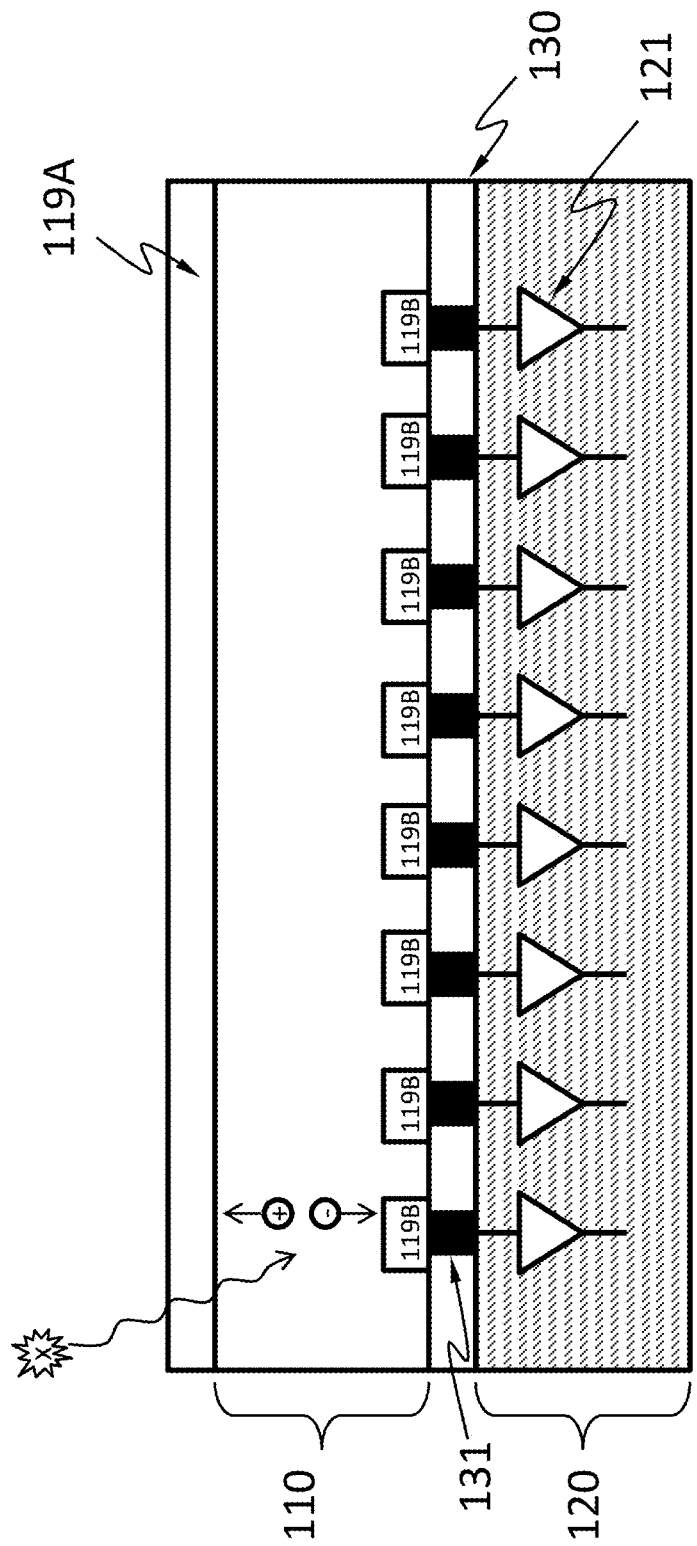
FIG. 11C schematically shows an alternative detailed cross-sectional view of the radiation detector.

As shown in an alternative detailed cross-sectional view of the radiation detector 100 in FIG. 11C, according to an embodiment, the radiation absorption layer 110 may include a resistor of a semiconductor material such as, silicon, germanium, GaAs, CdTe, CdZnTe, or a combination thereof, but does not include a diode. The semiconductor may have a high mass attenuation coefficient for the radiation of interest.

When the radiation hits the radiation absorption layer 110 including a resistor but not diodes, it may be absorbed and generate one or more charge carriers by a number of mechanisms. A particle of the radiation may generate 10 to 100000 charge carriers. The charge carriers may drift to the electrical contacts 119A and 119B under an electric field. The field may be an external electric field. The electrical contact 119B includes discrete portions. In an embodiment, the charge carriers may drift in directions such that the charge carriers generated by a single particle of the radiation are not substantially shared by two different discrete portions of the electrical contact 119B ("not substantially shared" here means less than 2%, less than 0.5%, less than 0.1%, or less than 0.01% of these charge carriers flow to a different one of the discrete portions than the rest of the charge carriers). Charge carriers generated by a particle of the radiation incident around the footprint of one of these discrete portions of the electrical contact 119B are not substantially shared with another of these discrete portions of the electrical contact 119B. A pixel 150 associated with a discrete portion of the electrical contact 119B may be an area around the discrete portion in which substantially all (more than 98%, more than 99.5%, more than 99.9% or more than 99.99% of) charge carriers generated by a particle of the radiation incident therein flow to the discrete portion of the electrical contact 119B. Namely, less than 2%, less than 0.5%, less than 0.1%, or less than 0.01% of these charge carriers flow beyond the pixel associated with the one discrete portion of the electrical contact 119B.

The electronics layer 120 may include an electronic system 121 suitable for processing or interpreting signals generated by the radiation incident on the radiation absorption layer 110. The electronic system 121 may include an analog circuitry such as a filter network, amplifiers, integrators, and comparators, or a digital circuitry such as a microprocessors, and memory. The electronic system 121 may include one or more ADCs. The electronic system 121 may include components shared by the pixels or components dedicated to a single pixel. For example, the electronic system 121 may include an amplifier dedicated to each pixel and a microprocessor shared among all the pixels. The electronic system 121 may be electrically connected to the pixels by vias 131. Space among the vias may be filled with a filler material 130, which may increase the mechanical stability of the connection of the electronics layer 120 to the radiation absorption layer 110. Other bonding techniques are possible to connect the electronic system 121 to the pixels without using vias.

Figure 12:
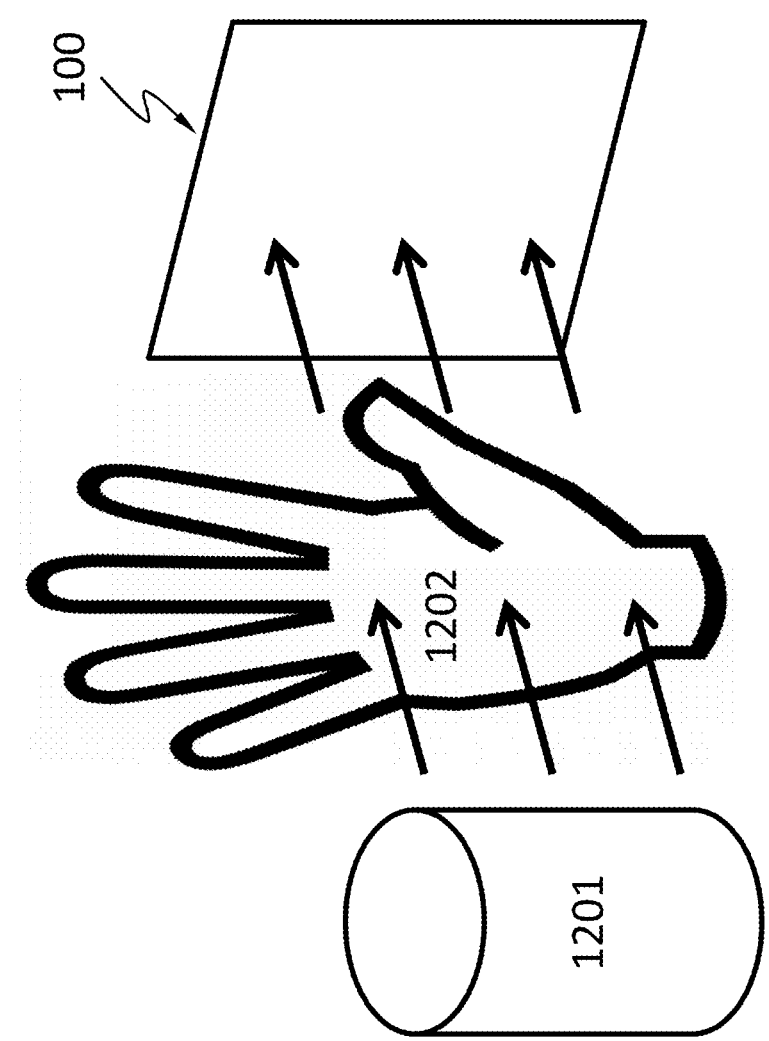

FIG. 12 schematically shows a system comprising the radiation detector 100 described herein. The system may be used for medical imaging such as chest X-ray radiography, abdominal X-ray radiography, etc. The system comprises a pulsed radiation source 1201 that emits X-ray. X-ray emitted from the pulsed radiation source 1201 penetrates an object 1202 (e.g., a human body part such as chest, limb, abdomen), is attenuated by different degrees by the internal structures of the object 1202 (e.g., bones, muscle, fat and organs, etc.), and is projected to the radiation detector 100. The radiation detector 100 forms an image by detecting the intensity distribution of the X-ray.

Figure 13:
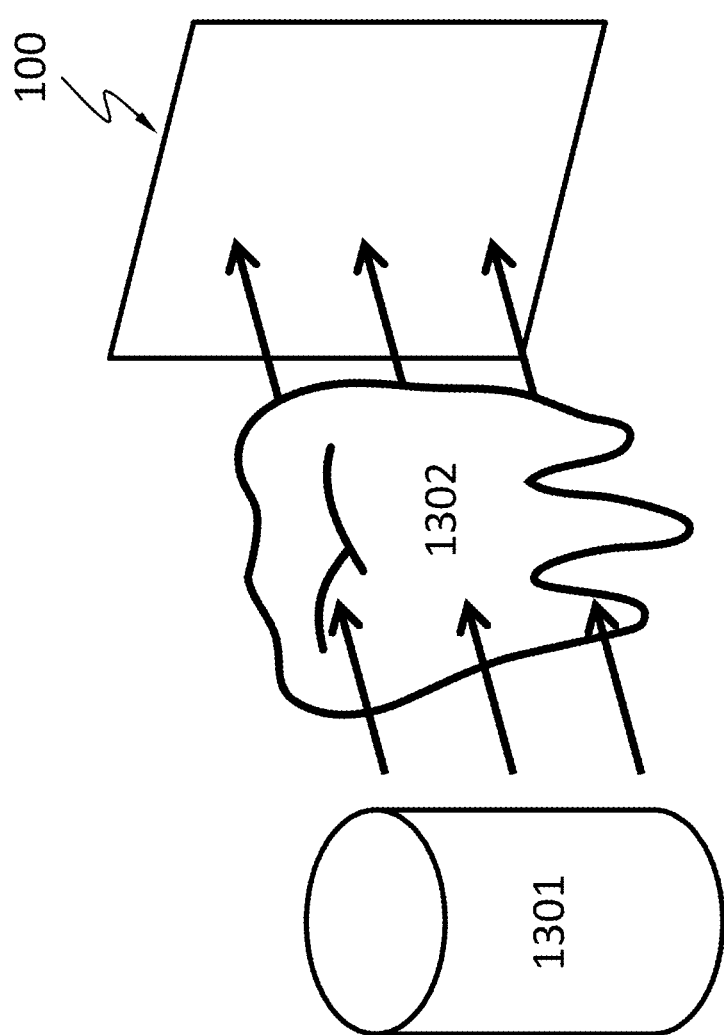

FIG. 13 schematically shows a system comprising the radiation detector 100 described herein. The system may be used for medical imaging such as dental X-ray radiography. The system comprises a pulsed radiation source 1301 that emits X-ray. X-ray emitted from the pulsed radiation source 1301 penetrates an object 1302 that is part of a mammal (e.g., human) mouth. The object 1302 may include a maxilla bone, a palate bone, a tooth, the mandible, or the tongue. The X-ray is attenuated by different degrees by the different structures of the object 1302 and is projected to the radiation detector 100. The radiation detector 100 forms an image by detecting the intensity distribution of the X-ray. Teeth absorb X-ray more than dental caries, infections, periodontal ligament. The dosage of X-ray radiation received by a dental patient is typically small (around 0.150 mSv for a full mouth series).

Figure 14:
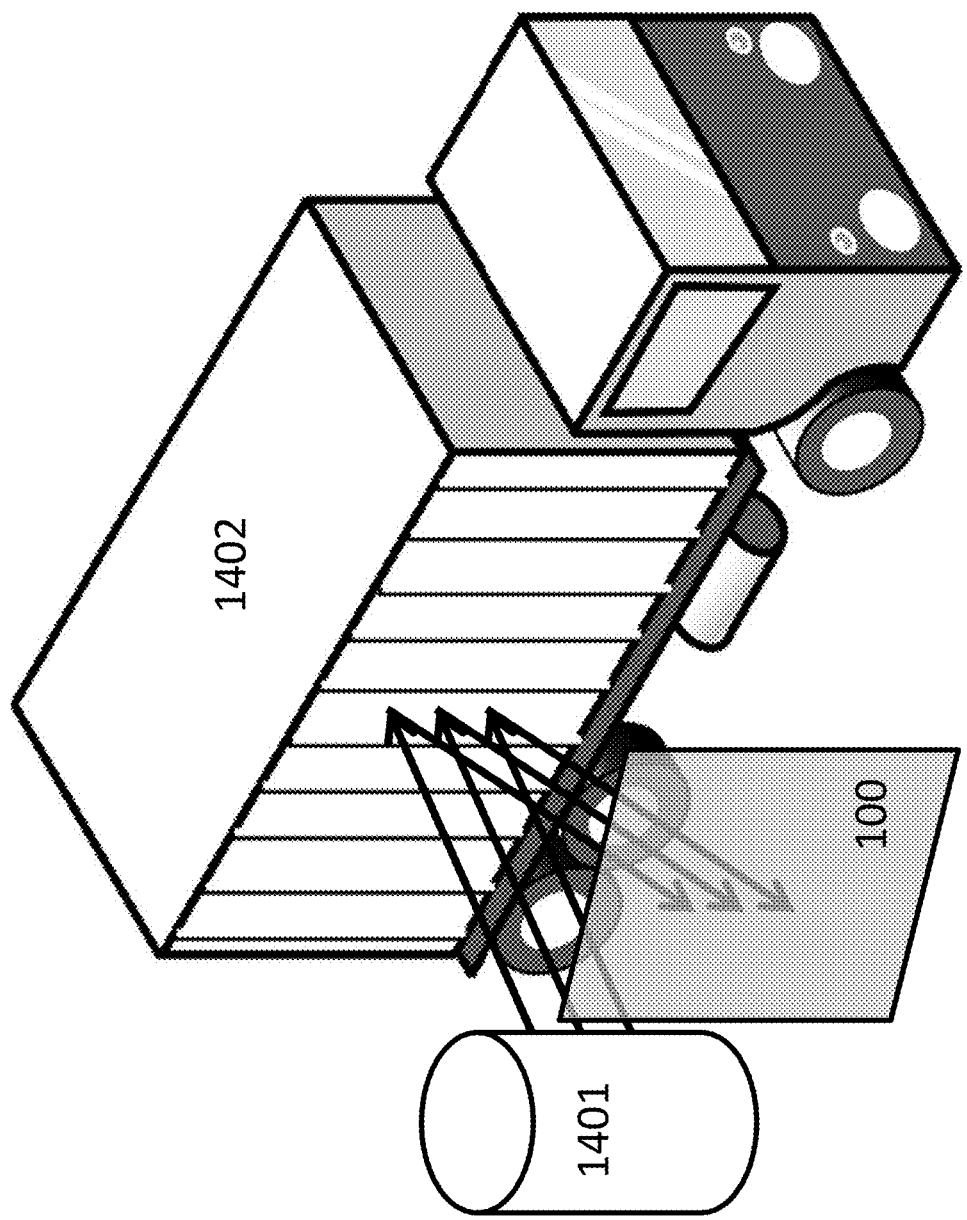

FIG. 14 schematically shows a cargo scanning or non-intrusive inspection (NII) system comprising the radiation detector 100 described herein. The system may be used for inspecting and identifying goods in transportation systems such as shipping containers, vehicles, ships, luggage, etc. The system comprises a pulsed radiation source 1401. Radiation emitted from the pulsed radiation source 1401 may backscatter from an object 1402 (e.g., shipping containers, vehicles, ships, etc.) and be projected to the radiation detector 100. Different internal structures of the object 1402 may backscatter the radiation differently. The radiation detector 100 forms an image by detecting the intensity distribution of the backscattered radiation and/or energies of the backscattered radiation.

Figure 15:
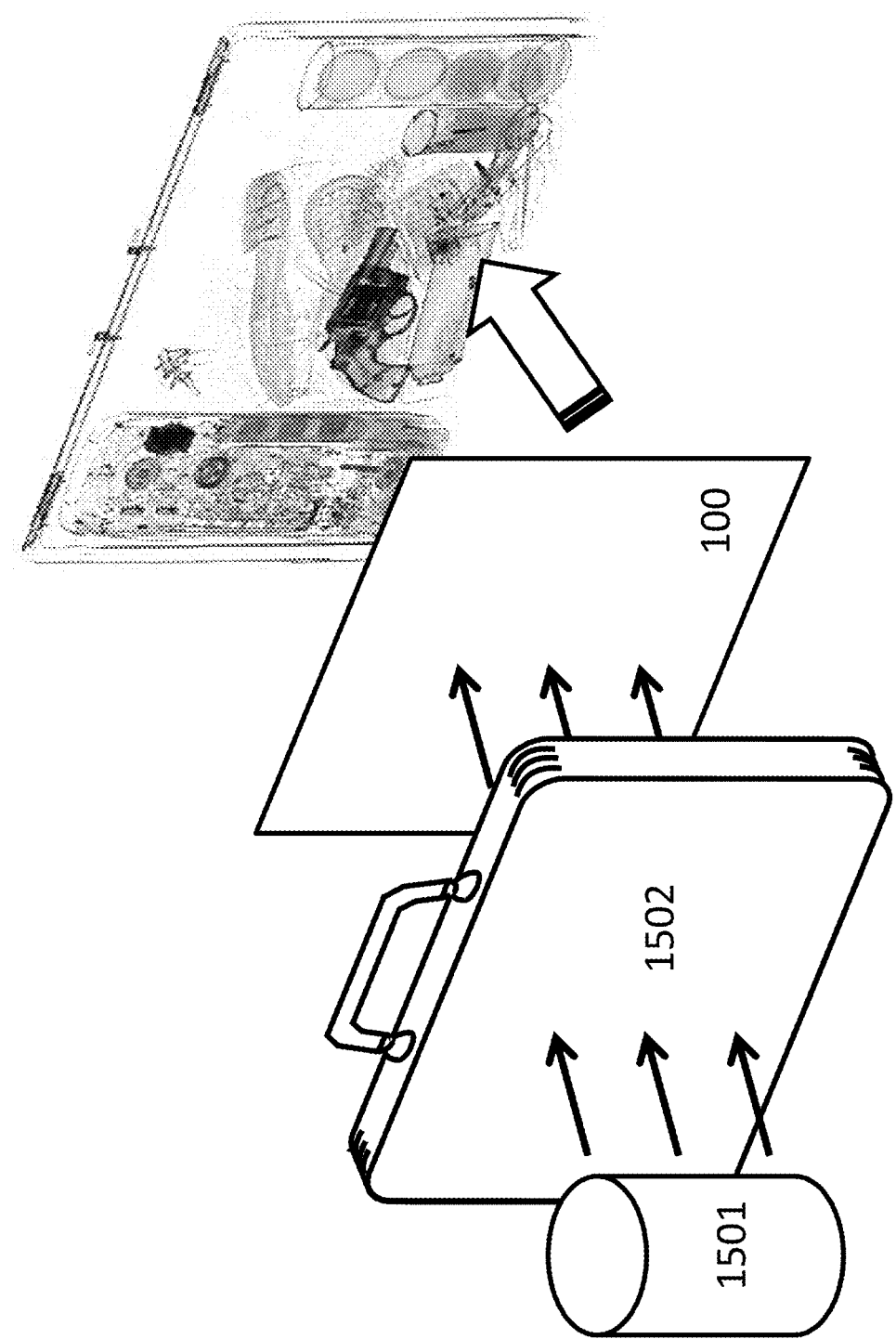

FIG. 15 schematically shows another cargo scanning or non-intrusive inspection (NII) system comprising the radiation detector 100 described herein. The system may be used for luggage screening at public transportation stations and airports. The system comprises a pulsed radiation source 1501 that emits X-ray. X-ray emitted from the pulsed radiation source 1501 may penetrate a piece of luggage 1502, be differently attenuated by the contents of the luggage, and projected to the radiation detector 100. The radiation detector 100 forms an image by detecting the intensity distribution of the transmitted X-ray. The system may reveal contents of luggage and identify items forbidden on public transportation, such as firearms, narcotics, edged weapons, flammables.

FIG. 16 schematically shows a full-body scanner system comprising the radiation detector 100 described herein. The full-body scanner system may detect objects on a person's body for security screening purposes, without physically removing clothes or making physical contact. The full-body scanner system may be able to detect non-metal objects. The full-body scanner system comprises a pulsed radiation source 1601. The radiation emitted from the pulsed radiation source 1601 may backscatter from a human 1602 being screened and objects thereon, and be projected to the radiation detector 100. The objects and the human body may backscatter the radiation differently. The radiation detector 100 forms an image by detecting the intensity distribution of the backscattered radiation. The radiation detector 100 and the pulsed radiation source 1601 may be configured to scan the human in a linear or rotational direction.

FIG. 17 schematically shows an X-ray computed tomography (X-ray CT) system. The X-ray CT system uses computer-processed X-rays to produce tomographic images (virtual "slices") of specific areas of a scanned object. The tomographic images may be used for diagnostic and therapeutic purposes in various medical disciplines, or for flaw detection, failure analysis, metrology, assembly analysis and reverse engineering. The X-ray CT system comprises the radiation detector 100 described herein and a pulsed radiation source 1701 that emits X-ray. The radiation detector 100 and the pulsed radiation source 1701 may be configured to rotate synchronously along one or more circular or spiral paths.

The pulsed radiation detector 100 described here may have other applications such as in an X-ray telescope, X-ray mammography, industrial X-ray defect detection, X-ray microscopy or microradiography, X-ray casting inspection, X-ray non-destructive testing, X-ray weld inspection, X-ray digital subtraction angiography, etc. It may be suitable to use this pulsed radiation detector 100 in place of a photographic plate, a photographic film, a PSP plate, an X-ray image intensifier, a scintillator, or another semiconductor X-ray detector.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A radiation detector, comprising:
pixels, and
a controller;
wherein each of the pixels is configured to detect radiation emitted from a pulsed radiation source;
wherein the pulsed radiation source is configured to emit radiation during ON periods and configured not to emit radiation during OFF periods;
wherein the controller is configured to determine that the pulsed radiation source is at one ON period of the ON periods or at one OFF period of the OFF periods;
wherein the controller is configured to cause the pixels to integrate signals with determination that the radiation source is at the one ON period and the controller is configured to cause the pixels not to integrate signals with determination that the radiation source is at the one OFF period;
wherein the radiation is X-ray.

2. The radiation detector of claim 1, wherein the signals during the ON periods comprise signals attributable to radiation from the pulsed radiation source and signals attributable to dark noise.

3. The radiation detector of claim 1, wherein the signals during the OFF periods comprise signals attributable to dark noise but not signals attributable to radiation from the pulsed radiation source.

4. The radiation detector of claim 1, wherein the controller is configured to cause the pixels to integrate signals during all of the ON periods.

5. The radiation detector of claim 1, wherein the controller is configured to cause the pixels not to integrate signals during all of the OFF periods.

6. The radiation detector of claim 1, wherein the controller is configured to process, during the OFF periods, signals of the pixels integrated.

7. The radiation detector of claim 1, wherein the controller is configured to digitize, during the OFF periods, signals of the pixels integrated.

8. The radiation detector of claim 1, wherein the controller is configured to reset signals of the pixels integrated.

9. The radiation detector of claim 1, wherein the radiation detector and the pulsed radiation source are synchronized to a same clock.

10. The radiation detector of claim 9, wherein the controller is configured to determine that the pulsed radiation source is at the one ON period or at the one OFF period based on a clock signal from the clock.

11. The radiation detector of claim 1, wherein the radiation detector comprises a device configured to detect an intensity of the radiation from the pulsed radiation source as a function of time.

12. The radiation detector of claim 11, wherein the device has a lower shot noise than the pixels.

13. The radiation detector of claim 11, wherein the controller is configured to determine that the pulsed radiation source is at the one ON period or at the one OFF period based on the intensity of the radiation.

14. The radiation detector of claim 1, wherein the controller is configured to determine that the pulsed radiation source is at the one ON period or at the one OFF period, using the pixels.

15. The radiation detector of claim 14, wherein the controller is configured to determine that the pulsed radiation source is at the one ON period or at the one OFF period, based on a combined signal of a plurality of the pixels.

16. The radiation detector of claim 1, wherein exposure of the pixels to the radiation is synchronized.

17. A system comprising the radiation detector of claim 1 and the pulsed radiation source.

18. The system of claim 17, wherein the system is configured to perform X-ray radiography on human chest or abdomen, to perform X-ray radiography on human mouth, to form an image using backscattered radiation, or to form an image using radiation transmitted through an object inspected.

19. The radiation detector of claim 1, wherein the controller is configured to cause the pixels to integrate the signals during two neighboring ON periods without resetting the signals between the two neighboring ON periods.

20. A radiation detector:
wherein the radiation detector is configured to detect radiation from a pulsed radiation source;
wherein the pulsed radiation source is configured to emit radiation during ON periods and configured not to emit radiation during OFF periods;
wherein the radiation detector is configured to determine that the pulsed radiation source is at one ON period of the ON periods or at one OFF period of the OFF periods;
wherein the radiation detector is configured to integrate signals with determination that the radiation source is at the one ON period and the controller is configured not to integrate signals with determination that the radiation source is at the one OFF period;
wherein the radiation is X-ray.

21. The radiation detector of claim 20, wherein the ON periods and the OFF periods have adjustable lengths.

22. The radiation detector of claim 20, wherein the signals during the ON periods comprise signals attributable to radiation from the pulsed radiation source and signals attributable to dark noise.

23. The radiation detector of claim 20, wherein the signals during the OFF periods comprise signals attributable to dark noise but not signals attributable to radiation from the pulsed radiation source.

24. A system comprising the radiation detector of claim 20 and the pulsed radiation source.

25. The system of claim 24, wherein the system is configured to perform X-ray radiography on human chest or abdomen, to perform X-ray radiography on human mouth, to form an image using backscattered radiation, or to form an image using radiation transmitted through an object inspected.

26. The radiation detector of claim 20, wherein the radiation detector is configured to integrate the signals during two neighboring ON periods without resetting the signals between the two neighboring ON periods.

* * * * *